US012765896B2

(12) United States Patent
Ghani et al.

(10) Patent No.: US 12,765,896 B2
(45) Date of Patent: Oct. 20, 2026

(54) DEVICES, SYSTEMS, AND METHODS FOR TREATING KIDNEY STONES

(71) Applicant: AMBU A/S, Ballerup (DK)

(72) Inventors: Khurshid Ghani, Ann Arbor, MI (US); Jeffrey Plott, Ann Arbor, MI (US)

(73) Assignee: AMBU A/S, Ballerup (DK)

( * ) Notice: Subject to any disclaimer, the term of this patent is extended or adjusted under 35 U.S.C. 154(b) by 906 days.

(21) Appl. No.: 17/607,734

(22) PCT Filed: Apr. 30, 2020

(86) PCT No.: PCT/US2020/030605
§ 371 (c)(1),
(2) Date: Oct. 29, 2021

(87) PCT Pub. No.: WO2020/223429
PCT Pub. Date: Nov. 5, 2020

(65) Prior Publication Data

US 2022/0218367 A1 Jul. 14, 2022

Related U.S. Application Data

(60) Provisional application No. 62/915,149, filed on Oct. 15, 2019, provisional application No. 62/841,635, filed on May 1, 2019.

(51) Int. Cl.
*A61B 17/22* (2006.01)
*A61B 1/00* (2006.01)
(Continued)

(52) U.S. Cl.
CPC .......... *A61B 17/22* (2013.01); *A61B 1/00091* (2013.01); *A61B 1/015* (2013.01);
(Continued)

(58) Field of Classification Search
CPC ..... A61B 17/22; A61B 1/00091; A61B 1/015; A61B 1/018; A61B 1/05; A61B 1/0676;
(Continued)

(56) References Cited

U.S. PATENT DOCUMENTS 1,770,045 A 7/1930 Shore et al.
2,421,449 A 6/1947 Zuber et al.
(Continued)

FOREIGN PATENT DOCUMENTS

CN 2912540 Y 6/2007
CN 109431438 A 3/2019
(Continued)

OTHER PUBLICATIONS

International Preliminary Report on Patentability received for PCT Patent Application No. PCT/US2020/030605, mailed on Nov. 11, 2021, 9 pages.
(Continued)

*Primary Examiner* — Anh Tuan T Nguyen
*Assistant Examiner* — Li-Ting Song
(74) *Attorney, Agent, or Firm* — Faegre Drinker Biddle & Reath LLP

(57) ABSTRACT

Provided herein are devices, systems, and methods for treating kidney stones. In particular, provided herein are endoscopic (e.g., ureteroscope) devices with improved properties, as well as systems, and related methods for use in treating kidney stones and other applications.

20 Claims, 48 Drawing Sheets

(51) Int. Cl.
*A61B 1/015* (2006.01)
*A61B 1/018* (2006.01)
*A61B 1/05* (2006.01)
*A61B 1/06* (2006.01)
*A61B 1/307* (2006.01)
*A61B 17/00* (2006.01)
*A61B 18/26* (2006.01)

(52) U.S. Cl.
CPC ................ *A61B 1/018* (2013.01); *A61B 1/05* (2013.01); *A61B 1/0676* (2013.01); *A61B 1/307* (2013.01); *A61B 2017/0034* (2013.01); *A61B 2017/22079* (2013.01); *A61B 18/26* (2013.01)

(58) Field of Classification Search
CPC .................... A61B 1/307; A61B 18/26; A61B 2017/22079; A61B 1/0008; A61B 1/00089
USPC .......................................................... 600/156
See application file for complete search history.

(56) References Cited

U.S. PATENT DOCUMENTS 3,060,972 A 10/1962 Sheldon
3,850,175 A 11/1974 Iglesias
4,580,551 A 4/1986 Siegmund et al.
4,651,718 A 3/1987 Collins
4,911,148 A 3/1990 Sosnowski et al.
4,950,278 A 8/1990 Sachse et al.
4,998,916 A 3/1991 Hammerslag et al.
5,089,895 A 2/1992 Fraker et al.
5,176,126 A 1/1993 Chikama
5,376,960 A 12/1994 Wurster
5,379,756 A 1/1995 Pileski et al.
5,418,566 A 5/1995 Kameishi
5,438,975 A 8/1995 Miyagi et al.
5,547,457 A 8/1996 Tsuyuki et al.
5,575,756 A * 11/1996 Karasawa ............ A61B 1/0014 600/156
5,688,222 A 11/1997 Hluchy et al.
5,830,401 A 11/1998 Prichard et al.
5,871,440 A 2/1999 Okada
5,966,168 A 10/1999 Miyazaki
6,004,263 A 12/1999 Nakaichi
6,110,104 A 8/2000 Suzuki et al.
6,156,049 A 12/2000 Lovato et al.
6,302,616 B1 10/2001 Takahashi
6,375,651 B2 4/2002 Grasso, III et al.
6,456,863 B1 9/2002 Levin et al.
7,455,806 B2 11/2008 Junger et al.
7,758,495 B2 7/2010 Pease et al.
7,766,819 B2 8/2010 Matsumoto
7,981,027 B2 7/2011 Miyagi et al.
8,182,422 B2 5/2012 Bayer et al.
8,485,966 B2 7/2013 Robertson
8,547,424 B2 10/2013 Ishii et al.
8,784,298 B2 7/2014 Fructus et al.
9,089,297 B2 7/2015 Heimberger
9,155,453 B2 10/2015 Kumar et al.
9,339,283 B2 5/2016 Carroux
9,393,033 B2 7/2016 Zerfas et al.
10,004,385 B2 6/2018 Bresco Torras et al.
10,307,176 B2 6/2019 Honda et al.
10,321,804 B2 6/2019 Jacobsen et al.
10,335,020 B2 7/2019 Oskin
10,492,662 B2 12/2019 Govrin et al.
10,631,716 B2 4/2020 Matthison-Hansen
11,864,736 B2 1/2024 Pereira et al.
2002/0193663 A1 12/2002 Matsuura
2002/0198551 A1 12/2002 Grant et al.
2003/0056540 A1 3/2003 Mukasa et al.
2003/0208209 A1 11/2003 Gambale et al.
2004/0199052 A1 10/2004 Banik et al.
2004/0242963 A1 12/2004 Matsumoto
2005/0070759 A1 3/2005 Armstrong
2005/0075538 A1 4/2005 Banik et al.
2005/0119527 A1 6/2005 Banik et al.
2005/0131279 A1 6/2005 Boulais
2005/0140068 A1 6/2005 Junger et al.
2005/0154262 A1 7/2005 Banik et al.
2005/0203341 A1 9/2005 Welker et al.
2005/0234499 A1 10/2005 Olson et al.
2006/0020165 A1* 1/2006 Adams ............... A61B 1/00142 600/157
2006/0173244 A1* 8/2006 Boulais .................. A61B 1/015 600/156
2006/0178556 A1 8/2006 Hasser et al.
2007/0049800 A1 3/2007 Boulais
2007/0129466 A1 6/2007 Kagawa et al.
2007/0135682 A1 6/2007 Miyagi et al.
2007/0249896 A1 10/2007 Goldfarb et al.
2007/0249907 A1 10/2007 Boulais
2008/0091074 A1* 4/2008 Kumar ................... A61B 1/012 600/156
2008/0194911 A1 8/2008 Lee
2008/0221393 A1 9/2008 Padget
2008/0242935 A1 10/2008 Inoue
2008/0249483 A1 10/2008 Slenker
2008/0266441 A1 10/2008 Ichimura
2008/0268559 A1 10/2008 Jung
2008/0287741 A1 11/2008 Ostrovsky
2009/0054728 A1 2/2009 Trusty
2009/0105542 A1 4/2009 Kitagawa et al.
2009/0177040 A1 7/2009 Lyons
2009/0209819 A1 8/2009 Kitagawa et al.
2010/0210905 A1 8/2010 Takeuchi et al.
2010/0217072 A1 8/2010 Kondoh et al.
2010/0217082 A1 8/2010 Ito et al.
2010/0280316 A1 11/2010 Dietz et al.
2010/0324367 A1 12/2010 Matsumoto et al.
2011/0034771 A1 2/2011 Konstorum
2011/0166419 A1 7/2011 Reif et al.
2011/0184233 A1 7/2011 Fructus et al.
2011/0202039 A1 8/2011 Schaaf
2011/0230718 A1 9/2011 Akui
2011/0251519 A1 10/2011 Romoscanu
2012/0002981 A1 1/2012 Park
2012/0071716 A1 3/2012 Fructus et al.
2012/0165608 A1 6/2012 Banik et al.
2013/0023729 A1 1/2013 Vazales et al.
2013/0030249 A1 1/2013 Vazales et al.
2013/0041223 A1 2/2013 Kato
2013/0090529 A1 4/2013 Boulais
2014/0114129 A1 4/2014 Peh
2014/0210976 A1 7/2014 Lin
2014/0221749 A1 8/2014 Grant et al.
2015/0305758 A1 10/2015 Batchelor et al.
2015/0366436 A1 12/2015 Iuel
2016/0051222 A1 2/2016 Imahashi
2016/0101254 A1 4/2016 Hansen
2016/0166320 A1 6/2016 Ciulla et al.
2016/0174819 A1* 6/2016 Ouyang ............. A61B 1/00098 600/105
2016/0213227 A1 7/2016 Osaki et al.
2017/0188794 A1* 7/2017 Ouyang ............. A61B 1/00066
2017/0215964 A1 8/2017 Harrah et al.
2017/0215965 A1 8/2017 Harrah et al.
2017/0238793 A1* 8/2017 Govrin ................... A61B 1/015
2018/0235441 A1 8/2018 Huang et al.
2018/0325357 A1 11/2018 Boulais
2019/0046223 A1 2/2019 Dayton et al.
2019/0133705 A1 5/2019 Riojas et al.
2019/0142266 A1 5/2019 Casarotto
2019/0175007 A1 6/2019 Sørensen et al.
2019/0175799 A1 6/2019 Hsu et al.
2019/0298321 A1 10/2019 Intintoli et al.
2020/0054196 A1 2/2020 Govrin et al.
2020/0138268 A1 5/2020 Matthison-Hansen et al.
2020/0196843 A1 6/2020 Tah et al.
2020/0383675 A1* 12/2020 Jung ...................... A61B 1/015
2021/0030261 A1 2/2021 Kress

(56) References Cited

U.S. PATENT DOCUMENTS

| | | | | |
|---|---|---|---|---|
| 2021/0085158 | A1* | 3/2021 | Ikuma | A61B 1/00068 |
| 2021/0137354 | A1 | 5/2021 | Bob et al. | |
| 2021/0186316 | A1* | 6/2021 | Thommen | A61B 1/07 |
| 2021/0386442 | A1* | 12/2021 | Heimberger | A61B 1/0052 |
| 2022/0000350 | A1 | 1/2022 | Heimberger et al. | |
| 2022/0053998 | A1* | 2/2022 | Ghani | A61B 18/26 |
| 2022/0167834 | A1* | 6/2022 | Titus | A61B 1/053 |
| 2023/0248434 | A1* | 8/2023 | Altshuler | A61B 1/00091 600/108 |

FOREIGN PATENT DOCUMENTS

| | | | | |
|---|---|---|---|---|
| CN | 208784694 | U | | 4/2019 |
| CN | 109875681 | A | | 6/2019 |
| CN | 110037646 | A | | 7/2019 |
| CN | 209154018 | U | | 7/2019 |
| CN | 209301083 | U | | 8/2019 |
| CN | 209346976 | U | | 9/2019 |
| CN | 209499675 | U | | 10/2019 |
| CN | 209864037 | U | | 12/2019 |
| CN | 210643992 | U | | 6/2020 |
| DE | 102018108843 | A1 | | 10/2019 |
| EP | 3669746 | A1 | | 6/2020 |
| GB | 383223 | A | | 11/1932 |
| GB | 2268883 | A | | 1/1994 |
| KR | 20190106355 | | * | 9/2019 |
| WO | 1996022739 | A1 | | 8/1996 |
| WO | 00/56387 | A1 | | 9/2000 |
| WO | 2004026125 | A1 | | 4/2004 |
| WO | 2012/060932 | A2 | | 5/2012 |
| WO | WO 2014/106511 | | | 7/2014 |
| WO | 2015058329 | A1 | | 4/2015 |
| WO | WO 2019/002186 | | | 1/2019 |
| WO | 2020150713 | A2 | | 7/2020 |
| WO | WO 2020/223429 | | | 11/2020 |
| WO | 2022/243553 | A2 | | 11/2022 |

OTHER PUBLICATIONS

International Search Report and Written Opinion of International Application No. PCT/US2020/030605, mailed Jul. 22, 2020, 10 pgs.

Examination and Search Report for Denmark Application No. DK PA202170265, mailed on Nov. 17, 2021, 7 pages.

Examination and Search Report for Denmark Application No. DK PA202170266, mailed on Dec. 15, 2021, 9 pages.

International Search Report and Written Opinion received for PCT Patent Application No. PCT/EP2022/063812, mailed on Nov. 22, 2022, 16 pages.

Extended search report in related European Application No. 20798662.1, dated Dec. 14, 2022, 8 pages.

* cited by examiner

A

- Stone mass = 194 mg
- Success rate 10/10

- Stone mass = 207 mg
- Success rate 10/10

- Stone mass = 422 mg
- Success rate 3/10

- Stone mass = 460 mg
- Success rate 0/10

B

- Stone mass = 194 mg
- Success rate 10/10

- Stone mass = 207 mg
- Success rate 10/10

- Stone mass = 422 mg
- Success rate 6/10

- Stone mass = 460 mg
- Success rate 9/10

DEVICES, SYSTEMS, AND METHODS FOR TREATING KIDNEY STONES

CROSS REFERENCE TO RELATED APPLICATION

This application claims priority to and the benefit of U.S. Provisional Application No. 62/841,635, filed May 1, 2019, and U.S. Provisional Application No. 62/915,149, filed Oct. 15, 2019, the contents of which are hereby incorporated by reference in their entireties.

FIELD

Provided herein are devices, systems, and methods for treating kidney stones. In particular, provided herein are endoscopic (e.g., ureteroscope) devices with improved properties, as well as systems, and related methods for use in treating kidney stones and other applications.

BACKGROUND

Kidney stone disease, also known as urolithiasis, is characterized by the presentation of a solid piece of material (known as a calculus or kidney stone) in the urinary tract. Kidney stones typically form in the kidney and leave the body in the urine stream. A small stone may pass without causing symptoms. If a stone grows to more than 5 millimeters (0.2 inches), it can cause blockage of the ureter resulting in severe pain in the lower back or abdomen. A stone may also result in blood in the urine, vomiting, or painful urination. About half of people who experience a kidney stone will have another stone within ten years.

Treatments for kidney stories include medical expulsive therapy (e.g., using alpha adrenergic blockers (such as tamsulosin) or calcium channel blockers (such as nifedipine)), extracorporeal shock wave lithotripsy (ESWL), ureteroscopic surgery, and percutaneous nephrolithotomy surgical procedures.

However, existing technologies are limited by potential side effects and incomplete stone removal. Accordingly, a need exists for improved methods of treating kidney stones.

SUMMARY

Provided herein are devices, systems, and methods for treating kidney stones. In particular, provided herein are endoscopic (e.g., ureteroscope) devices with improved properties, as well as systems, and related methods for use in treating kidney stones and other applications.

The devices described herein solve a number of problems with existing endoscopic devices, for example, by improving visualization of stones when an instrument is in the working channel, reducing intrarenal pressure, eliminating the need for a basket for stone repositioning, providing the option of symmetrical working channels for better targeting stones, and providing suction that sucks the stone, stabilizes the stone, and evacuates stone dust and debris.

For example, in some embodiments, provided herein is an endoscopic device (e.g., ureteroscope) comprising an end (e.g., tip) (e.g., defined herein as the distal end but also can be defined as the proximal end, depending on perspective), the distal end comprising: a) a first channel (e.g., configured for delivery and/or removal of fluid and a laser or configured for suction); and b) a second channel (e.g., configured for delivery of fluid and a laser or configured to remove fluid via suction), wherein the second channel exits the distal end on a different plane than the first channel (e.g., the first and second channel exits are in different planes with respect to the plane created by the distal end of the endoscopic device), and wherein the exit of the first or second channel comprises a suction port. In some embodiments, each channel has an opening substantially planar (i.e., greater than 90% of its area is on the single plane). In some embodiments, the plane of the first channel exit is in the plane of the distal end. In some embodiments, the plane of the distal end is perpendicular to the longitudinal axis of the endoscopic device. In some embodiments, the plane of the distal end is substantially perpendicular (+/−10 degrees of perpendicular) to the longitudinal axis of the longitudinal axis of the endoscopic device.

Further provided is an endoscopic device comprising a working (e.g., tip or distal) end, the distal end comprising: a) a first channel configured for delivery of fluid and optionally a laser; and b) a second channel configured to remove fluid via suction and optionally delivery of a laser, wherein the second channel exits the end on a different plane than the first channel and wherein the exit of the second channel comprises a suction port, and wherein the first and second channels are configured to prevent stones from occluding the suction port.

Also provided is an endoscopic device comprising a distal end, the distal end comprising: a) a first channel configured for delivery of fluid and optionally a laser; and b) a second channel configured to remove fluid via suction and optionally delivery of a laser, wherein the second channel exits the distal end on a different plane than the first channel and wherein the exit of the second channel comprises a suction port, wherein the suction port comprises a plurality of protrusions and/or depressions.

Yet other embodiments provide an endoscopic device comprising a distal end, the distal end comprising: a) a first channel configured for delivery of fluid and optionally a laser; and b) a second channel configured to remove fluid via suction and optionally delivery of a laser, wherein the second channel exits the distal end on a different plane than the first channel and wherein the exit of the second channel comprises a suction port, and wherein the suction port is on a protrusion.

Certain embodiments provide an endoscopic device comprising a distal end, the distal end comprising: a) a first channel having an exit in a first plane configured for delivery of fluid and optionally a laser; and b) a second channel having an exit in a second plane and wherein the exit of the second channel comprises a suction port and wherein said second channel is optionally configured for delivery of a laser.

In some embodiments, the distal end of the endoscopic device further comprises one or more additional components, for example, a camera and/or a light. In some embodiments, the camera is positioned above the suction port, partially above the suction port, level, partially below the suction port or below the suction port (e.g., in a cut out of the distal region). In some embodiments, the location of the camera and the light are interchangeable. In some embodiments, the light comprises a fiber optic filament or one or more LEDs. In some embodiments, the camera and the light are located proximal or distal to each other. In some embodiments, the camera is located on a plane above the plane of the working channel and/or suction port. In some embodiments, the working channel and/or suction port are angled out and away from the camera (e.g., at an angle of 20-160 degrees about an X-axis of the endoscopic device and/or 5-25 degrees about a line on the YZ-plane of the endoscopic device, although other angles are specifically contemplated).

In some embodiments, the endoscopic device further comprises a laser slider configured to move the laser about the longitudinal axis of the endoscopic device. In some embodiments, actuation of the laser slider unclogs stone fragments stuck in the working channel.

In some embodiments, the suction port comprises one or more anti-clog elements (e.g., including but not limited to, one or more of the port or channel in operable communication with the port comprising a smaller inner diameter than suction tubing in operable communication with the port, a mesh material that covers the opening, a bar or beam that covers the opening, and/or one or more protrusions or depressions adjacent to the opening). In some embodiments, the anti-clog elements prevent occlusion of the suction port, working channel or suction channel by a kidney stone or fragments thereof. In some embodiments, the distal opening of the first and/or second channel comprises a mesh or filter. In some embodiments, the filter is pivotable and/or flexible (e.g., to allow an instrument to fit through the opening) or comprises an opening for an instrument.

In some embodiments, the region of the distal end surrounding the suction port is flat, rounded, concave, or protruded. In some embodiments, the first and second channels are located adjacent or distal to each other. In some embodiments, the exit of the first channel and/or exit of second channel is substantially planar or substantially in the first and/or second plane. In some embodiments, the suction port and working channel are on symmetrical planes relative to the longitudinal axis of the endoscopic device. In some embodiments, the suction port and working channel are on asymmetrical planes relative to the longitudinal axis of the endoscopic device. In some embodiments, the suction port and working channel are interchangeable. In some embodiments, the channel configured for a laser is also used for removal of fluid via suction.

In some embodiments, the distal end further comprises one or more flow diverters configured to direct fluid flow towards the second or suction channel. In some embodiments, the flow diverter is located at the opening of the first or second channel. Devices may comprise one or more (e.g., 1, 2, 3, 4, or more) flow diverters of the same or different types located at the same or different locations relative to the first and second channels. In some embodiments, the flow diverters are in fluid communication with the first and/or second channels.

In some embodiments, the first and second channels have the same or different diameters. For example, in some embodiments, the first channel has an inner diameter of 0.4 to 0.6 mm (e.g., sized for a laser) and the second channel has an inner diameter of 1.1 to 1.3 mm sized for suction and/or irrigation).

The present disclosure is not limited to particular materials for constructing endoscopic devices or an end of the endoscopic device. In some embodiments, at least a portion of the distal end is constructed of a compliant material (e.g., including but not limited to, a silicone elastomer, a thermoplastic elastomer, or a foam). In some embodiments, the compliant material surrounds or comprises the suction port. In some embodiments, the compliant material is configured to deform to fit the shape of a kidney stone. In some embodiments, the compliant material has a Shore hardness of between OO10 and A40. In some embodiments, at least a portion of the distal end is constructed of a material selected from, for example, a thermoplastic, a metal, or a combination thereof (e.g., a material with a hardness of greater than A40 on the Shore hardness scale).

In some embodiments, the endoscopic device comprises an outer housing (e.g., outer housing and/or outer jacket) surrounding an interstitial space, wherein the distal end or distal portion of the endoscopic device comprises one or more interstitial flow openings in fluid communication with the interstitial space, wherein the interstitial flow openings are configured to deliver fluids or suction through such interstitial space; and a fluid port and/or suction component (e.g. located at the proximal end of the endoscopic device (e.g., in the handle) or another location).

Also provided herein is an endoscopic device, comprising: a) an outer housing surrounding an interstitial space, wherein the distal end or distal portion of the endoscopic device comprises one or more interstitial flow openings in fluid communication with the interstitial space, wherein the interstitial flow openings are configured to deliver fluids or suction through the interstitial space. In some embodiments, the outer housing further comprises a fluid port in fluid communication with the interstitial space. In some embodiments, the fluid port is located at the proximal end of the endoscopic device (e.g., in the handle). In some embodiments, the endoscopic device further comprises a working channel. In some embodiments, the interstitial space comprises one or more of a sensor wire, a camera wire, a pull wire, a light wire, or a fiber optic cable or wire.

Further provided is an endoscopic device comprising a distal end, the distal end comprising: a) a first channel or opening configured for delivery of fluid; and b) a second channel or opening configured to remove fluid via suction, wherein the second channel exits the distal end on a different plane than said first channel, and wherein the distal end further comprises one or more flow diverters, wherein the flow diverters are configured to direct fluid flow from the first channel or opening towards the second channel or opening.

Further embodiments provide a system, comprising: a) an endoscopic device as described herein; and b) an irrigation delivery system and a suction system. In some embodiments, the system further comprises a temperature sensor and/or pressure sensor at the distal end. In some embodiments, the system further comprises a computer system configured to adjust the irrigation delivery system and the suction system based on readings from the temperature and pressure sensors. In some embodiments, the adjusting maintains temperature and pressure of the fluid at the distal end within a range that reduces or prevents side effects due to excess pressure and/or temperature during use. In some embodiments, the adjusting increases or decreases suction to securely hold a stone and/or release a stone for repositioning within the kidney or extraction through the ureter.

Yet other embodiments provide a method of ablating a kidney stone, comprising: introducing an endoscopic device as described herein into the ureter of a subject; b) advancing the endoscopic device to a kidney or ureteral stone; and c) ablating the stone using the endoscopic device.

Additional embodiments are described herein.

DESCRIPTION

Provided herein are devices, systems, and methods for treating kidney stones. In particular, provided herein are endoscopic (e.g., ureteroscope) devices with improved properties, as well as systems, and related methods for use in treating kidney stones and other applications.

Significant absorption of irrigation fluid may occur during endoscopic stone surgery and cause hypothermia, pain, and fluid overload. Maintenance of a low intrarenal pressure may decrease the risks of these occurrences. In addition, with increasing use of high-power laser settings for lithotripsy, the potential exists to induce thermal tissue damage. In vitro studies have demonstrated that temperature elevation sufficient to cause thermal tissue damage can occur with certain laser and irrigation settings.

Clinicians currently address this by using a ureteral access sheath to allow fluid drainage between the sheath and the ureteroscope, as these procedures can be lengthy and prolonged high intra-renal pressures can increase the risk of hemorrhage, infection, sepsis, collecting system perforation, and fluid absorption. Other techniques, including repositioning of kidney stones from the lower pole location into an upper pole location before fragmentation and optionally extraction of the generated fragments, may improve results, as well as provide a stone sample for analysis obviating the need to employ a stone basket.

However, the use of a ureteral access sheath is associated with risk of injury to the ureter, extra costs and time to insert this device, and need for ureteral stent placement after its use, causing significant pain and urinary symptoms for the patient. Furthermore, use of a basket for stone repositioning and retrieval can be difficult and time consuming.

The present disclosure addresses these limitations by providing suction, stone stabilization, and stone removal through a suction channel of a ureteroscope. In some embodiments, provided herein is a ureteroscope comprising a distal end, the distal end comprising: a) a channel configured for delivery of one or more of fluid, suction, or a laser; and b) a further channel comprising a suction port that is configured to remove fluid via suction. In some embodiments, the channels exit the distal end of the ureteroscope on the same or different planes of plane of the distal end of the device (e.g., the plane of the distal end perpendicular to the longitudinal axis of the ureteroscope). The ureteroscope, through the configuration of the channel exits, reduces clogging of the suction port by stones or stone fragments.

While the present disclosure is exemplified with a ureteroscope, the compositions and methods described herein find use with any minimally invasive medical device, including but not limited to, endoscopic devices (e.g., flexible endoscopes), ureteroscopes, and the like.

Figure 1A:
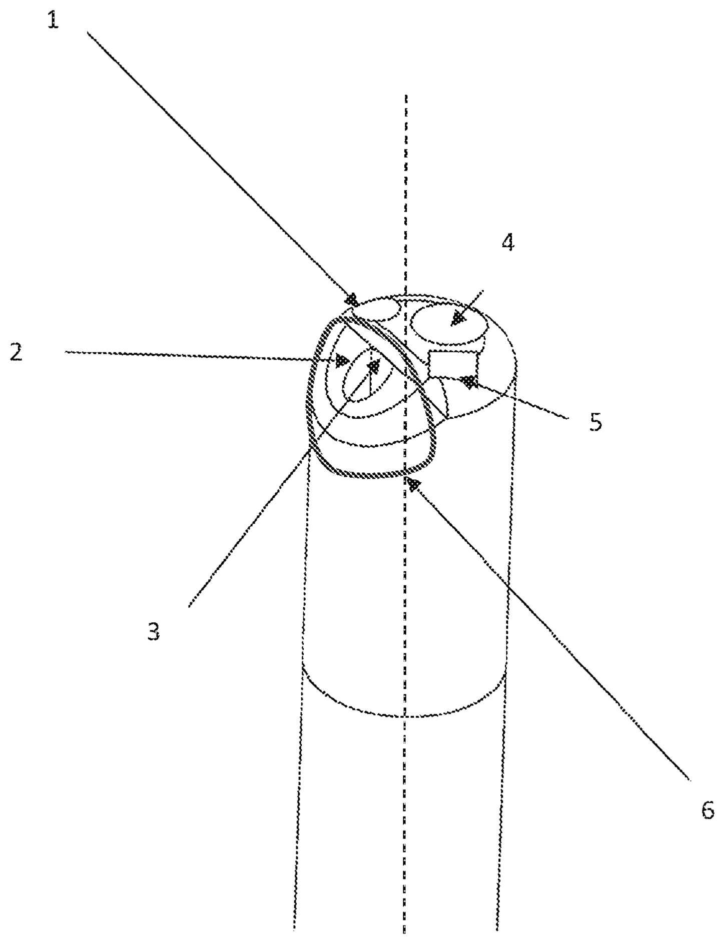
FIG. 1A-D show exemplary devices of embodiments of the present disclosure.

Exemplary devices and their use are shown in FIGS. 1-18. Referring to FIG. 1A, shown is a ureteroscope tip comprising light 1, suction port 2, anti-clog inlet or feature 3, working (e.g., laser and/or irrigation) channel 4, camera 5, and region 6, which optionally may be made of compliant material. The dashed line represents the longitudinal axis of the ureteroscope. The working channel 4 is presented on the distal end of the ureteroscope tip in a plane perpendicular to the longitudinal axis of the ureteroscope. Suction port 2 is presented on a different plane that the working channel 4, for example at a 20 to 70 degree angle relative to the plane of the working channel 4 (although the invention is not limited to these particular dimensional relationships). In some embodiments, the suction port 2 is on a different plane from the camera 5. In some embodiments, this prevents the camera image from becoming blocked by a stone or stone fragments during fluid suction through the suction channel. As a stone or stones collect in front of the suction channel, they will tend to angle away from the camera field of view, helping to mitigate the full camera obstruction so the clinician can continue to see where they are in the kidney. In some embodiments, region 6 is not made of compliant material, but rather a non-compliant material. In the device shown in FIG. 1A, the face surrounding the suction port is flat. The light 1 serves to illuminate the working area.

In FIG. 1 and other images described herein, working channel 4 and other channels are exemplified as having circular, oval, or other geometries. However, the present disclosure is not limited to a particular geometry of channel, channel openings, or ports. Other shapes are specifically contemplated. For example, in some embodiments, to minimize the outer diameter of the insertable portion while maximizing the open area of the working or other channel, it may be preferable to use a non-circular cross-sectional shape.

The present disclosure is not limited to a particular lighting technology. In some embodiments, commercially available lights are utilized, including, for example, one or more LED lights or fiber optic filaments. In some embodiments, the light illuminates the entire circumference of ureteroscope (e.g., using fiber optic technology to generate a ring of light).

The working channel 4 provides a port for a laser and/or fluid delivery. In some embodiments, the channel 4 is able to accommodate both a laser and a fluid delivery component (e.g., during ablation). The present disclosure is not limited to particular types and/or sources of lasers. In some embodiments, the laser is a Holmium:Ytrrium Aluminium Garnet (Ho:YAG) laser, although other lasers such as the Thulium Fiber Laser (TFL) may be used. In some embodiments, the laser fiber is a 230 μm or 365 μm fiber, or a 150 μm fiber or smaller if using the TFL.

In some embodiments, the fluid delivery component is saline (e.g., in a bag) delivered via tubing. In some embodiments, the fluid delivery component is held on a stand, pressurized, or connected to an automated delivery system.

In some embodiments, the camera 5 provides a real-time view of the working area to the operator of the device, displayed on a user interface that may be connected by wire or wirelessly to the camera. In some embodiments, the camera is a video camera. The present disclosure is not limited to particular camera technologies.

In some embodiments, where the region 6 is made of compliant material, the material is selected to provide a level of compliance that allows region 6 to conform to the shape of a stone when a stone contacts region 6.

The anti-clog inlet 3 (described in more detail below) prevents clogging of the suction port and/or suction channel (not shown in FIG. 1A) by large stones or stone fragments.

Figure 1B:
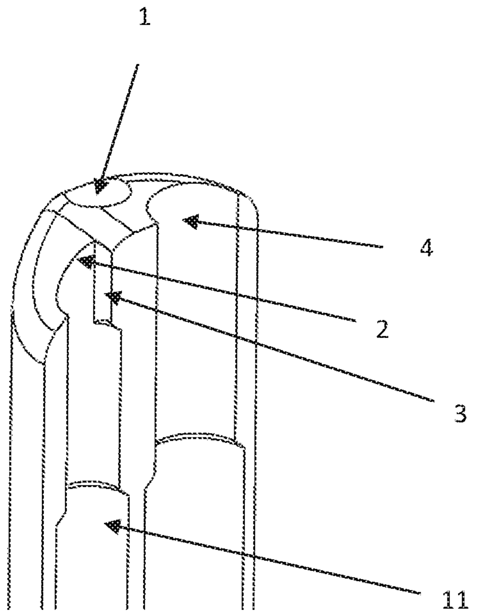

FIG. 1B shows a cross-section cut-out view of the device of FIG. 1A. Shown is light 1, suction port 2, anti-clog inlet 3, working channel 4, and suction channel 11. The suction channel 11 and working channel continue through the device and exit the proximal end of the device (not shown). In some embodiments, the diameter of the suction channel 11 and/or working channel 4 are narrower near the distal opening as shown in FIG. 1B. This first narrowing can assist with device assembly, providing a hard stop for tubing used for the suction channel 11 and/or working channel 4. In some embodiments, this first narrowing matches the inner diameter of the tubing connected to the ureteroscope tip. In some embodiments, the tubing has metallic braiding (e.g., stainless steel or nitinol) in the wall to prevent distal channel kinking during ureteroscope articulation. An additional narrowing, such as seen with anti-clog inlet 3, can be utilized to prevent stone fragments of a certain size from entering suction channel II. This can act to reduce the chances for suction channel 11 to clog with fragments during the procedure. In other embodiments, channel diameters are constant throughout the device.

Figure 1C:
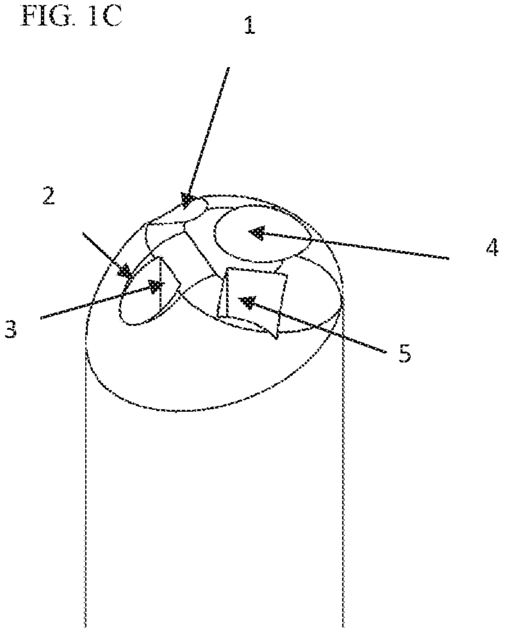

FIG. 1C shows an exemplary device similar to FIG. 1A with a rounded, concave face surrounding the suction port 2 rather than a flat face as shown in FIG. 1A. Shown is light 1, suction port 2, anti-clog inlet 3, working channel 4, and camera 5. In this embodiment, the working channel 4 on the rounded surface is presented on a plane substantially perpendicular to the longitudinal axis of the ureteroscope with the suction port 2 residing on a different plane.

Figure 1D:
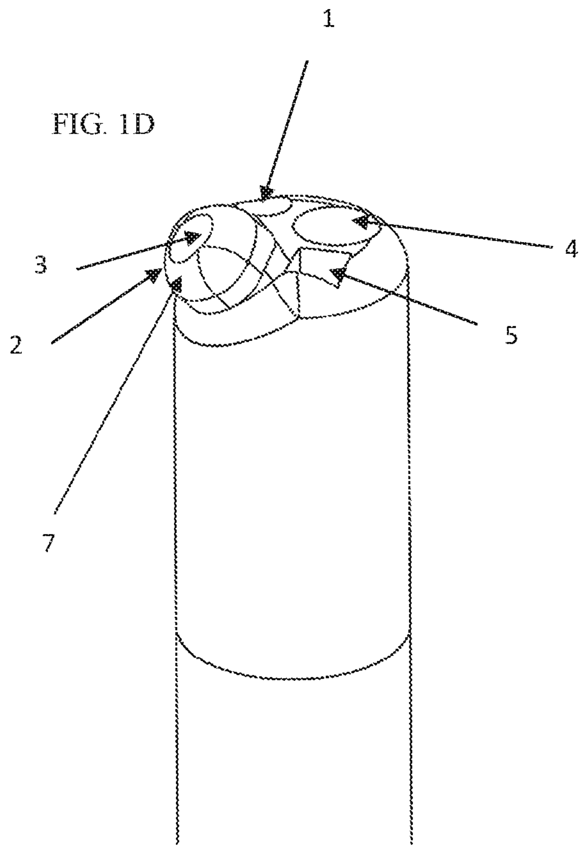

FIG. 1D shows an exemplary device similar to FIG. 1A where the suction port is presented on a protrusion 7 comprising suction port 2 and anti-clog inlet 3. Placing the suction port on a protrusion aids in isolating the suction port from the camera and reduces the risk of a stone obstructing the view of the camera. In some embodiments, protrusion 7 is constructed of a compliant material. The protrusion 7 may be of any shape or length that accommodates the inlet 3.

Still referring to FIG. 1A-C, in some embodiments, the camera 5 is positioned above the surface of the suction port 2 and the suction port 2 is angled such that if a stone attaches to the suction port there is a reduced risk of vision impairment. The tip of the ureteroscope is preferably rounded and smooth to make insertion into the ureter easier.

Figure 2A:
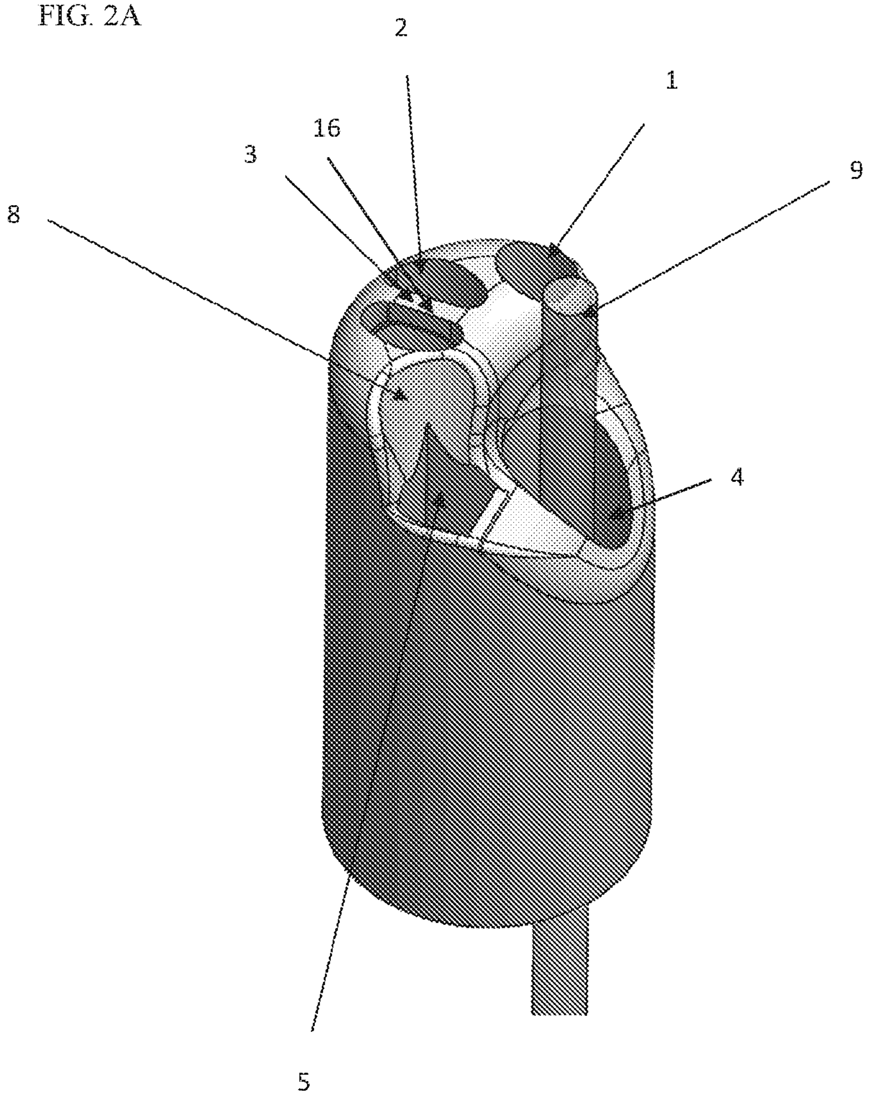
FIG. 2A-C show alternative embodiments of devices of the present disclosure.

Now referring to FIG. 2A, shown is an alternative design, where a camera 5 is positioned below the suction port 2. This allows the user to see when a stone is engaged with the suction port. Still referring to FIG. 2A, in some embodiments, the camera is in camera cut-out region 8. As desired, multiple cameras may be employed. Also shown in FIG. 2A is anti-clog inlet 3, suction ports 2, light 1, and laser 9 residing in working channel 4. Still referring to FIG. 2A, the camera cut-out region 8 is shown as a notch in the distal end of the device. The camera 5 is shown placed at the bottom of cut-out region 8 below suction port 2. Still referring to FIG. 2A, suction port 2 and anti-clog inlet 3 are shown as separate openings separated by a bar 16 that lead to suction channel 11 (not shown). Still referring to FIG. 2A, the working channel 4, shown with laser 9, exits the device on a different plane than suction port 2. In this instance, suction port 2 is in a plane substantially perpendicular to the longitudinal axis of the ureteroscope and the working channel is in a non-perpendicular plane. In some embodiments, (not shown in FIG. 2A), the working channel is on the perpendicular plane and on a different plane than the suction port.

Figure 2B:
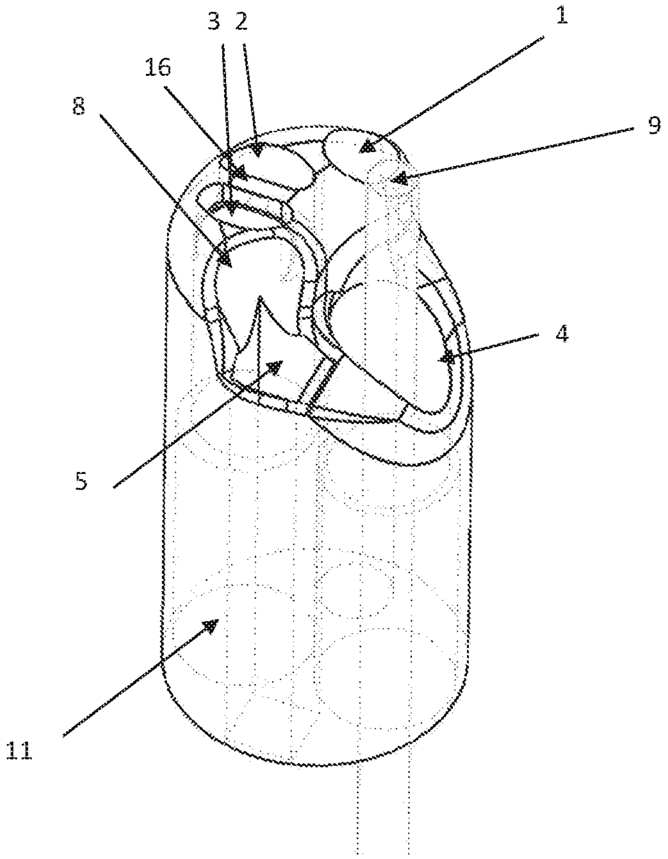

FIG. 2B provides a transparent view of embodiment shown in FIG. 2A, showing positioning of laser 9 in working channel 4. Also shown is camera 5, camera cut-out region 8, anti-clog inlet 3, suction ports 2, suction channel 11, light 1, and laser 9. As shown in FIG. 2B, suction port 2 and anti-clog inlet 3 are both in fluid communication with suction channel 11. Still referring to FIG. 2B, laser 9 is shown inserted in working channel 4.

Figure 2C:
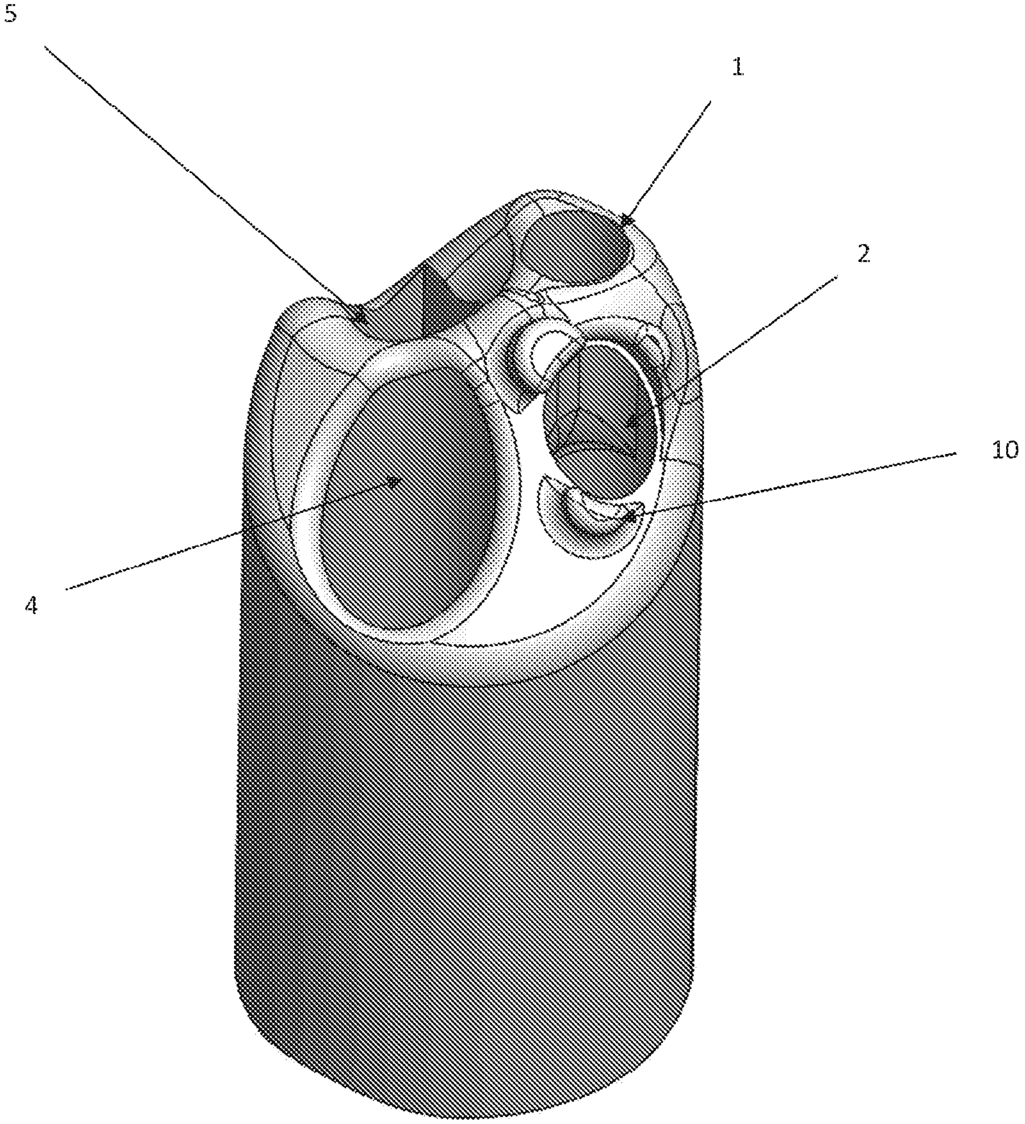

FIG. 2C shows an alternative embodiment where the anti-clog feature comprises a plurality of protrusions or depressions 10 surrounding the entrance of the suction port 2 that prevents the suction port from getting occluded by a kidney stone or fragment thereof. In FIG. 2C, two protrusions and I depression are shown, although other configurations are specifically contemplated. The present disclosure is not limited to a particular shape or configuration of protrusions/depressions 10.

In some embodiments, devices comprise symmetrical (e.g., comprising symmetry around the bending axis of the device) working channels 4 that interchangeably serve as suction or laser/irrigation channels (See e.g., below descriptions of FIGS. 3A-B and 4A-B). For example, in some embodiments, a user can select either channel for suction or laser/irrigation use depending on the laterality of the kidney (e.g. right or left side), region of the kidney, shape or location of stone, or other factors. This provides for improved visibility and access to stones using a single device. In some embodiments, channels are used interchangeably during a single procedure (e.g., a user switches the function of a channel during a single procedure on a single stone or multiple stones).

Figure 3A:
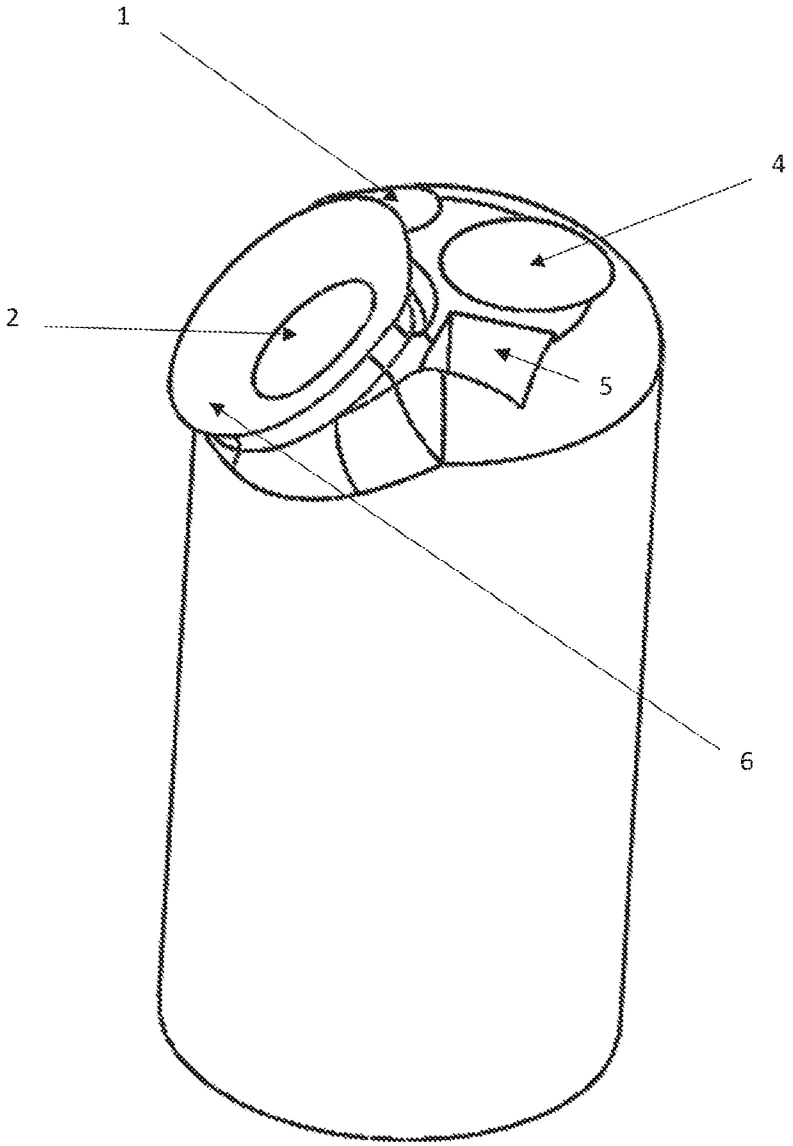
FIG. 3A-B show alternative embodiments of devices of the present disclosure comprising compliant regions.
Figure 3B:
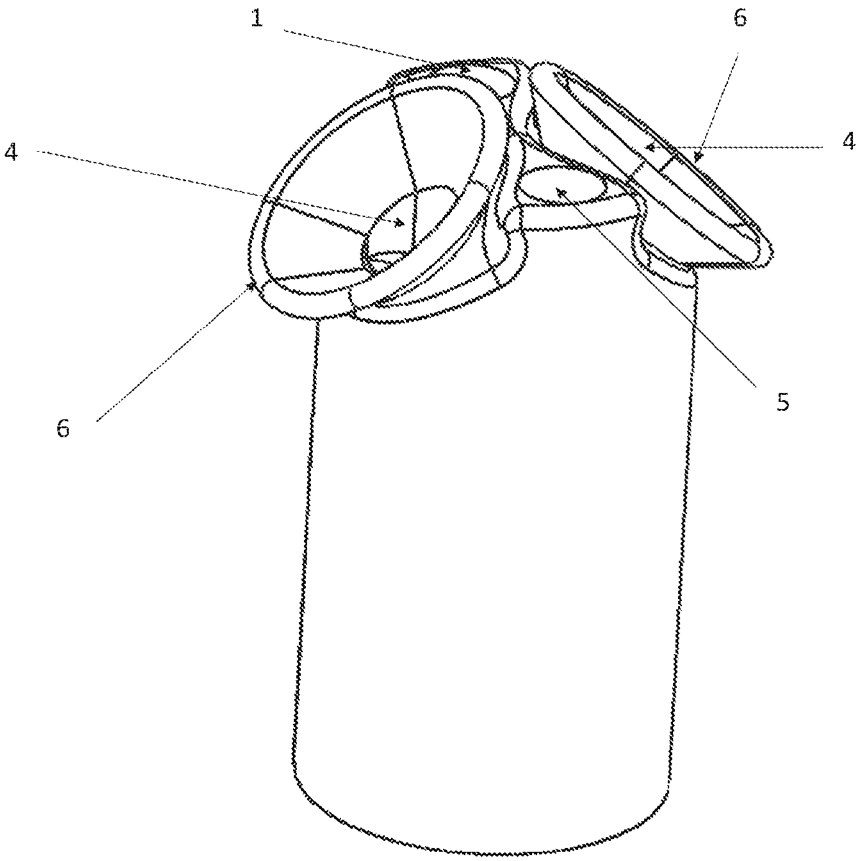

Now referring to FIG. 3A-B, shown is an alternative embodiment of a device comprising a compliant region 6 in a suction cup shape. In some embodiments, suction cup shaped compliant region 6 is designed to conform to irregularly shaped kidney stones so they can be secured and moved to a desired location in the kidney.

FIG. 3A shows a device where the compliant region 6 in a suction cup shape surrounds or comprises suction port 2. As shown in FIG. 3A, working channel 4 does not include a compliant region 6. Still referring to FIG. 3A, the suction port comprising a suction cup shaped compliant region is on a different plane than the exit of working channel 4. Also shown is light 1 and camera 5, which are on a different plane than suction port 2 and the same plane as the exit of working channel 4.

FIG. 3B shows an alternative device with two symmetrical working channels 4 that each comprise a suction cup shaped compliant region 6. As shown in FIG. 3B, the exits of symmetrical working channels 4 are on different, but symmetrical planes. In this embodiment, the exits of working channels 4 are on a plane that is not perpendicular to the longitudinal axis of the device. Also shown are light 1 and camera 5, which are on a different plane than the exits of working channels 4.

Figure 4A:
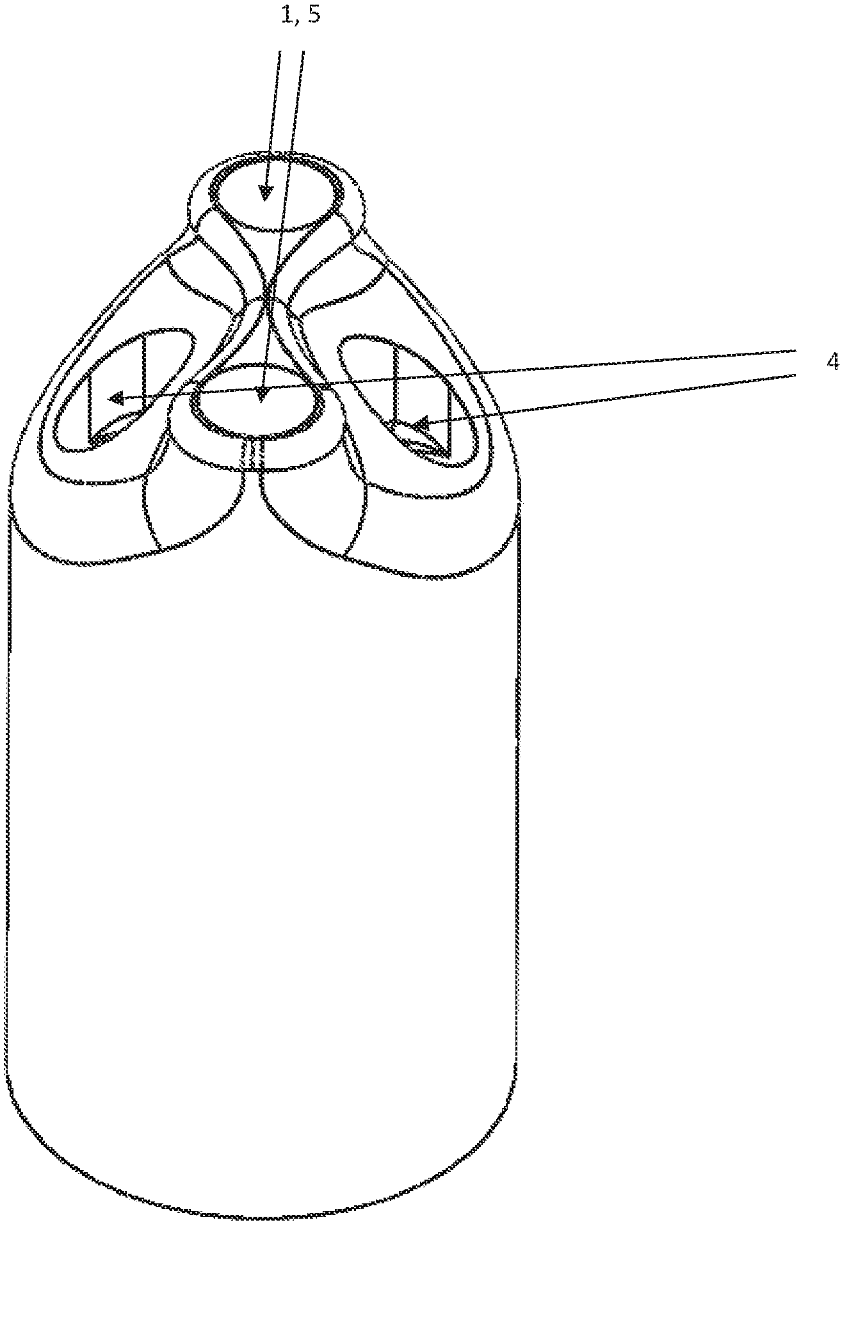
FIG. 4A-B show alternative embodiments of devices of the present disclosure comprising symmetrical channels.
Figure 4B:
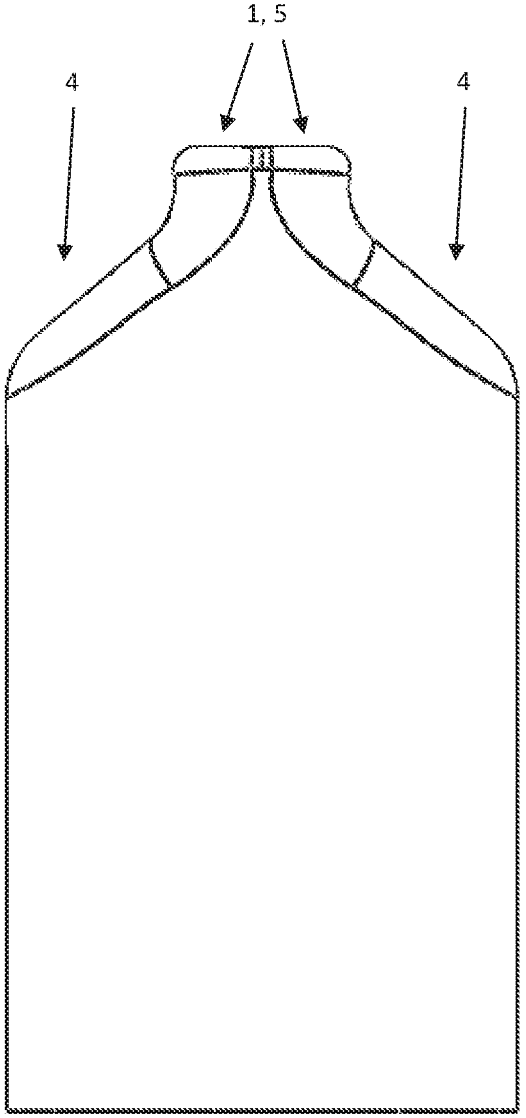

Now referring to FIG. 4A-B, shown are exemplary devices with symmetrical working channels 4 and interchangeable light 1 and camera 5 locations. In some embodiments, the light 1 and camera 5 are independently placed in either of the locations shown as 1, 5 in FIG. 4A-B. While not being limited to specific device designs, it is contemplated that devices described herein independently comprise both a camera 5 and light 1. In symmetrical devices such as those shown in FIG. 4A-B, the device is constructed in either of the two possible configurations for light 1 and camera 5 (e.g., the light is located at either the top or bottom location of FIG. 4A labeled as 1, 5 and the camera 5 is located at the other location not comprising a light 1).

FIG. 4A shows a device with symmetrical working channels/suction ports 4 and interchangeable light 1 and camera 5 locations. As shown in FIG. 4A, the exits of working channels 4 are in different, symmetrical planes on opposite sides of the device, although other symmetrical configurations are specifically contemplated. Still referring to FIG. 4A, the exits of working channels 4 are in a plane that is not perpendicular to the longitudinal axis of the device, although other plane geometries are specifically contemplated. Still referring to FIG. 4A, interchangeable light 1 and camera 5 locations 1, 5 are shown on the same plane, although other configurations are specifically contemplated. In FIG. 4A, the light 1 and camera 5 locations are in a plane perpendicular to the longitudinal axis of the device, although other geometries are specifically contemplated.

FIG. 4B shows a side view of the device of FIG. 4A. Shown are working channels 4 and interchangeable light 1 and camera 5 locations. The side view of FIG. 4B illustrates the symmetry of the exits of working channels 4 around the longitudinal axis of the device. The exits of working channels 4 are perpendicular to the plane of view and are thus not visible, however the locations of the exits are labelled. Still referring to FIG. 4B, the light 1 and camera 5 locations are also perpendicular to the plane of view and are thus not visible (see labels on FIG. 4B that mark the interchangeable locations of light 1 and camera 5). The side view further illustrates that light 1 and camera 5 are on a plane perpendicular to the longitudinal axis of the device.

Figure 5:
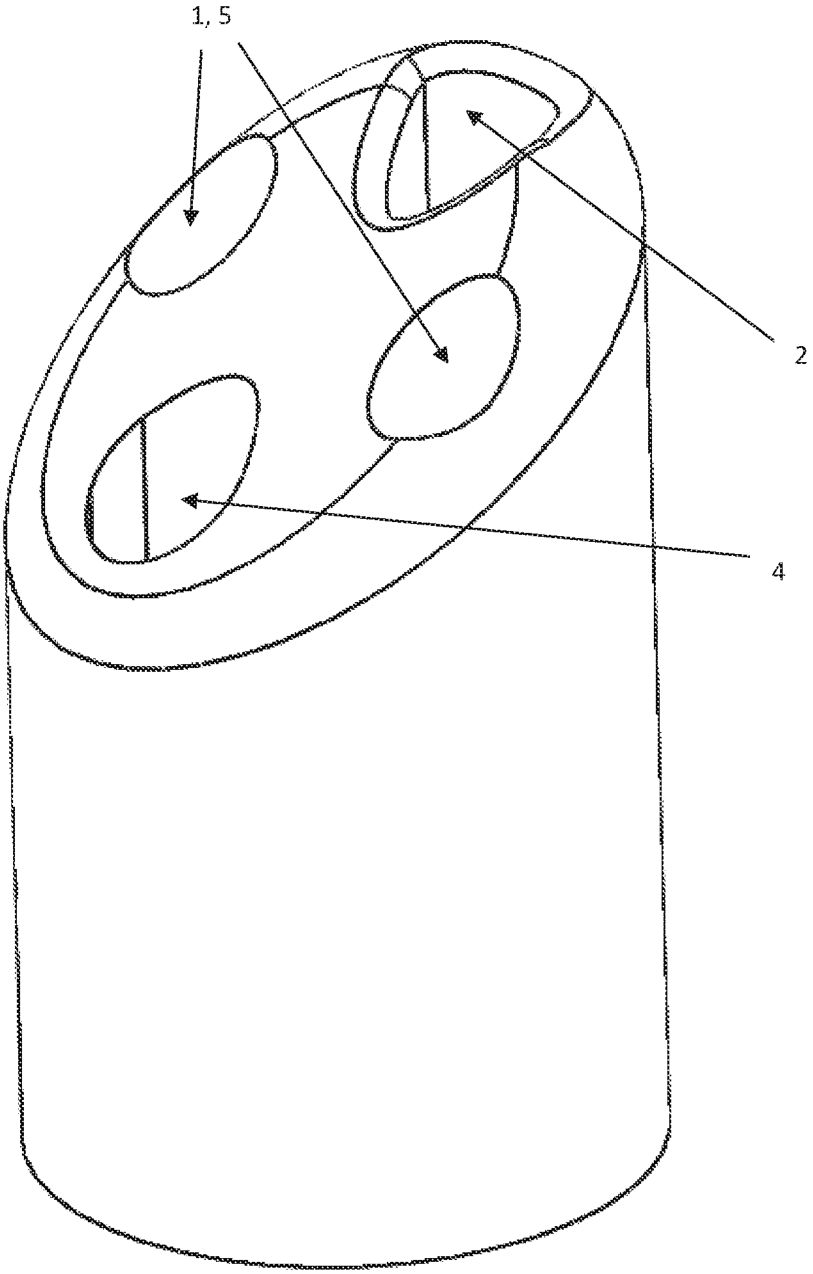
FIG. 5 shows an alternative embodiment of a device of the present disclosure.

Now referring to FIG. 5, shown is an alternative embodiment of a device comprising suction port 2, working channel 4 and interchangeable light 1 and camera 5 locations that exit the distal end on a single plane that is not perpendicular to the longitudinal axis of the device. In some embodiments, the light 1, suction port 2, working channel 4, and camera 5 all exit the device on the same plane. In some embodiments, the top edge of camera 5 protrudes from the plane in a perpendicular direction and thus is on a plane parallel to and above the plane that the suction port 2 and working channel 4 exit the device on, although the device is not limited to such a configuration. In some embodiments, the location of the suction port 2 and working channel 4 are switched.

Figure 6A:
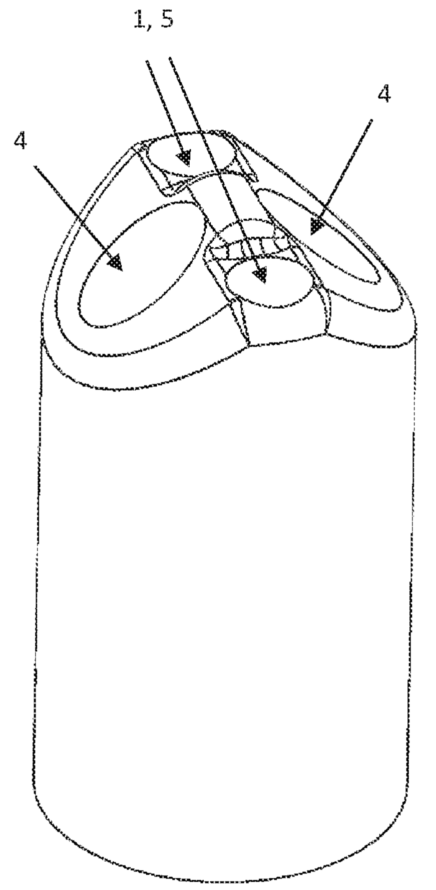
FIG. 6A-C show alternative embodiments of devices of the present disclosure comprising planar channels.
Figure 6B:
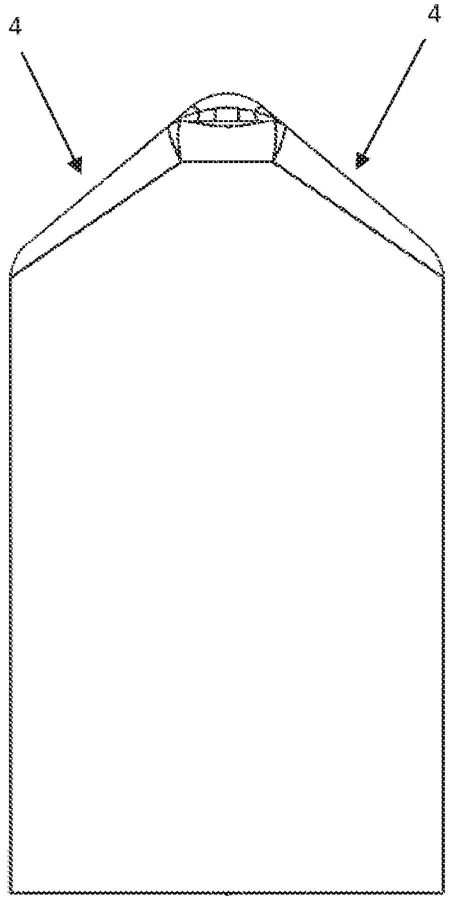
Figure 6C:
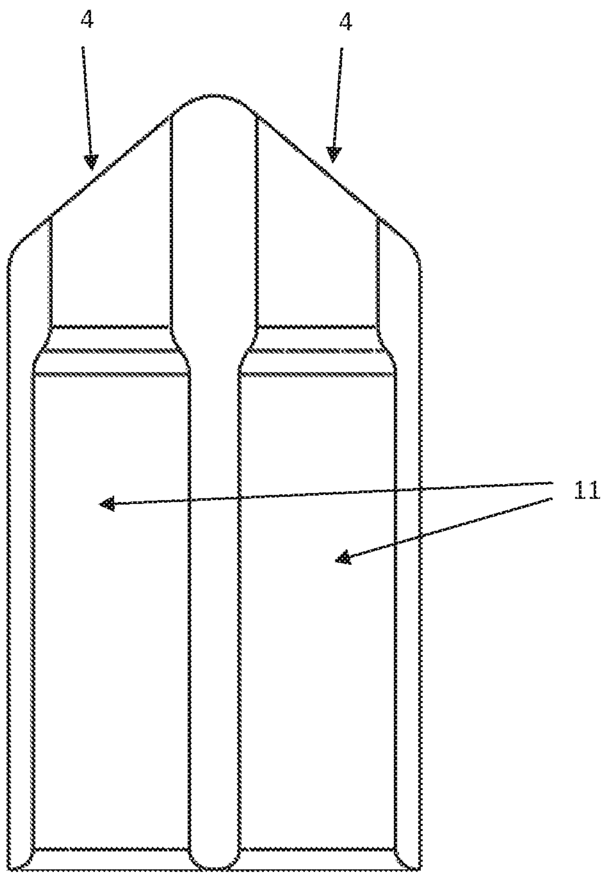

Now referring to FIG. 6A-C, shown is an alternative embodiment of a device where the suction port 2 and exit of working channel 4 are each substantially in a plane or are planar. As used herein, the term "substantially in a plane" or "substantially in the plane" in reference to an opening or exit of a channel or port of a device described herein refers to an opening or exit that is at least 90% (e.g., at least 90%, 91%, 92%, 93%, 94%, 95%, 96%, 97%, 98%, 99% or 100%) in a single plane (or substantial plane). For example, as shown in FIG. 6A, the exits of working channels 4 are substantially in a single plane because the entire exit area of working channels 4 shown in FIG. 6A are in the plane that the opening exits the device on. This is further illustrated in the side view shown in FIG. 6B and the cut-out view of FIG. 6C, where the entire opening of working channel 4 is in the plane that working channel 4 exits the device on.

As used herein, the term "substantially planar" when used in reference to an opening or exit of a channel or port of a device described herein refers to an opening or port that is at least 90% (e.g., at least 90%, 91%, 92%, 93%, 94%, 95%, 96%, 97%, 98%, 99% or 100%) planar throughout the entire opening or port. For example, the exits of working channels 4 shown in FIG. 6A-C are substantially planar (e.g., substantially in the same plane across the entire exit or opening). This definition tolerates some curvature of the opening around a plane (e.g., a curvature that follow the shape of a curved surface of the device).

Not all openings on the single device need to be in the same plane or a plane with the same angle relative to the longitudinal or perpendicular axis of the device in order to be individually substantially in a plane or planar. For example, in the device shown in FIG. 6A, each of the planes that the two working channels 4 exit the device on could be at a different angle relative to the longitudinal or perpendicular axis of the device (not shown in FIG. 6A), and each be considered to be substantially in the plane and substantially planar.

FIG. 6A shows a device comprising symmetrical working channels 4 and interchangeable light 1 and camera 5 locations. In this embodiment, the working channels are planar and substantially in a plane, although exits need not be symmetrical to be planar or in a plane. As shown in FIG. 6A, the exits of working channels 4 are in different, symmetrical planes on opposite sides of the device, although other symmetrical (or non-symmetrical) configurations are specifically contemplated. Still referring to FIG. CA, the exits of working channels 4 are in a plane that is not perpendicular to the longitudinal axis of the device, although other plane geometries are specifically contemplated. Still referring to FIG. CA, interchangeable light 1 and camera 5 locations 1, 5 are shown on the same plane, although other configurations are specifically contemplated. In FIG. 6A, the light 1 and camera 5 locations are in a plane perpendicular to the longitudinal axis of the device, although other geometries are specifically contemplated.

FIG. 6B shows a side view of the device of FIG. 6A. The exits of working channels 4 are shown as substantially in the plane. As shown, the entire exit of both working channels 4 are planar and in the plane of device. The opening or exit of working channels 4 is flush with the plane across the entire plane. The light 1 and camera 5 are in a plane perpendicular to the longitudinal axis of the device and are thus out of the field of view.

FIG. 6C shows a cut-out view of the device of FIG. 6A-B. Shown are working channels 4 and channels 11. In this embodiment, because the working channels 4 are symmetrical, channels 11 serve interchangeably as channels for laser/irrigation or suction. FIG. 6C additionally illustrates that the exits of working channels 4 are planar and in the plane of the exit. Still referring to FIG. 6C, shown is an embodiment where working channels 4 narrow near the exit, although other channel configurations are specifically contemplated.

Figure 7A:
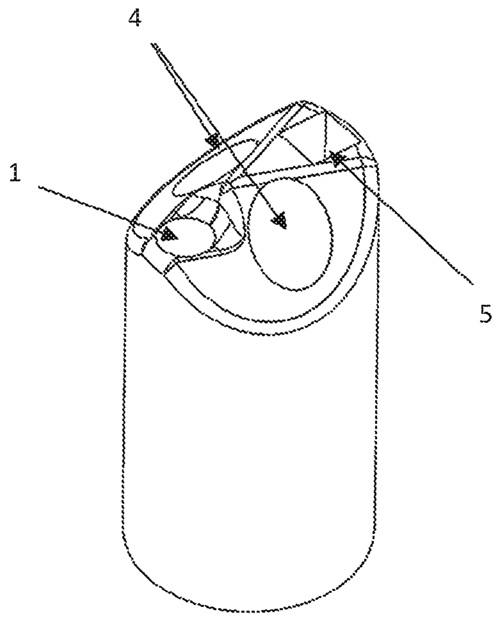
FIG. 7A-E show alternative embodiments of devices of the present disclosure.
Figure 7B:
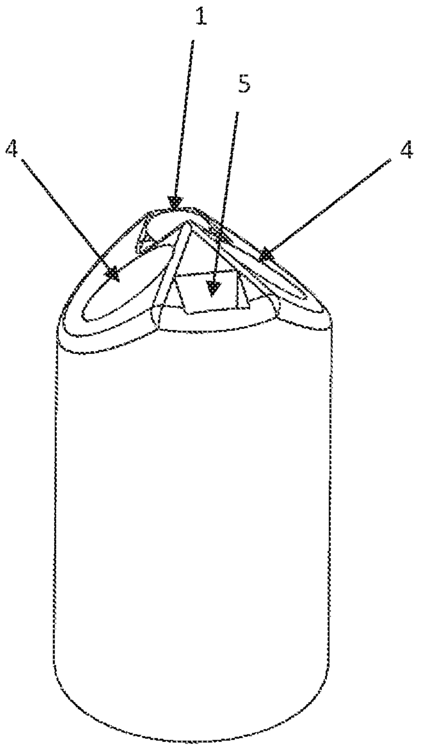
Figure 7C:
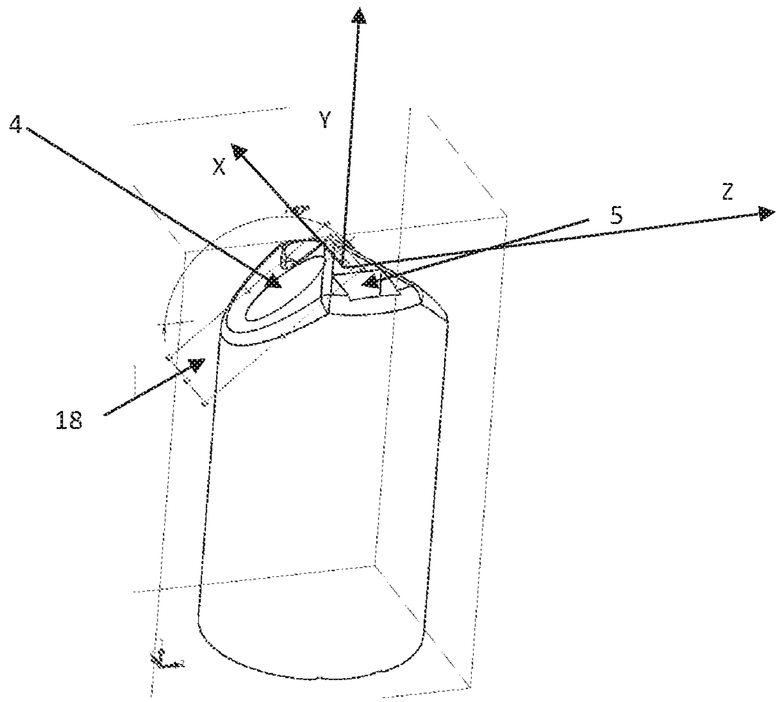
Figure 7D:
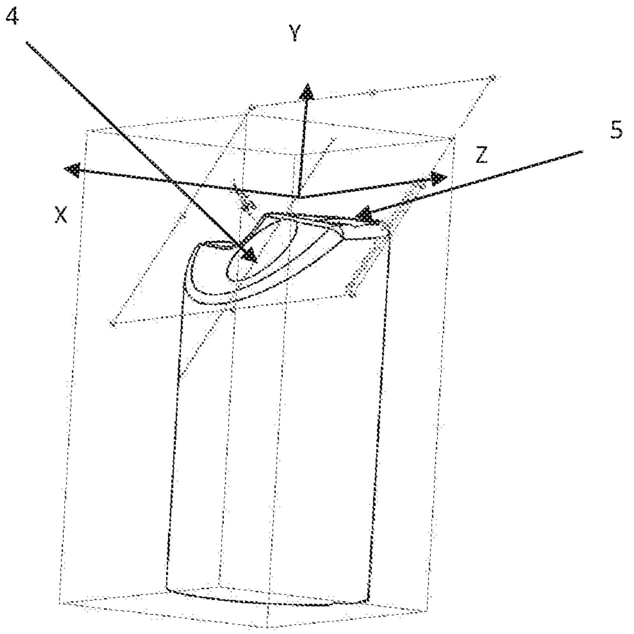

Now referring to FIG. 7A-E, shown is an alternative embodiment of a device where the camera 5 is on a plane above the working channels 4 and the working channels 4 are angled out and away from the camera (e.g., at an angle of 120-160 degrees (e.g., +/−1, 5, 10, 15, or 20%) about the X-axis, and/or 5-25 degrees (e.g., +/−1, 5, 10, 15, or 20%) about the YZ-plane, although other degrees of rotation are specifically contemplated (See e.g., FIG. 7C-D for an illustration of rotations around axes of an exemplary device). In some embodiments, this configuration prevents the stone from impeding the view from the camera when the stone is engaged with the suction port or working channel.

FIG. 7A shows a device with symmetrical working channels 4, light 1, and camera 5. The camera 5 is on its own plane above the plane of the working channels 4 and perpendicular to the longitudinal axis of the device, although the camera need not be on a perpendicular plane. In the view shown in FIG. 7A, the light is shown as recessed below the working channels 4 and camera 5, although other configurations of light 1 are specifically contemplated.

FIG. 7B shows a further view of the device of FIG. 7A from the side looking from the perspective of camera 5 down to light 1. The view of FIG. 7B illustrates that the plane of camera 5 is above the plane of the light 1 and working channels 4. The exits of working channels 4 shown in FIG. 7A-B are shown as symmetrical and substantially planar and substantially in the plane.

FIG. 7C shows a side view of the device of FIG. 7A-B illustrating the 140 degree rotation of the exits of working channels 4 away from the camera 5 about the X-axis. In FIG. 7C, the Y-axis, as labelled, points in the plane of the camera view. The X-axis, as labelled, points into the page. As shown in FIG. 7C, the plane 18 of the exit of working channel 4 is rotated 140 degrees about the X-axis (see labels of FIG. 7C for directions of each axis).

FIG. 7D shows a view of the device of FIG. 7A-B showing a 15 degree rotation of the exits of working channels 4 about a line positioned on the YZ-plane (see labels of FIG. 7D for directions of each axis). In order to illustrate rotation around a line on the YZ-plane, the device of FIG. 7D is rotated to a different view than the device of FIG. 7C. The rotation is marked with a curve. FIG. 7D illustrates the rotation of the working channel 4 away from camera 5. In combination with the rotation around the X-axis shown in FIG. 7C, the working channel is angled and moved to improve the view from camera 5 when a stone is engaged with the working channel 4. For example, when a stone is engaged with working channel 4, it will not obstruct or completely obstruct the view obtained from camera 5.

Figure 7E:
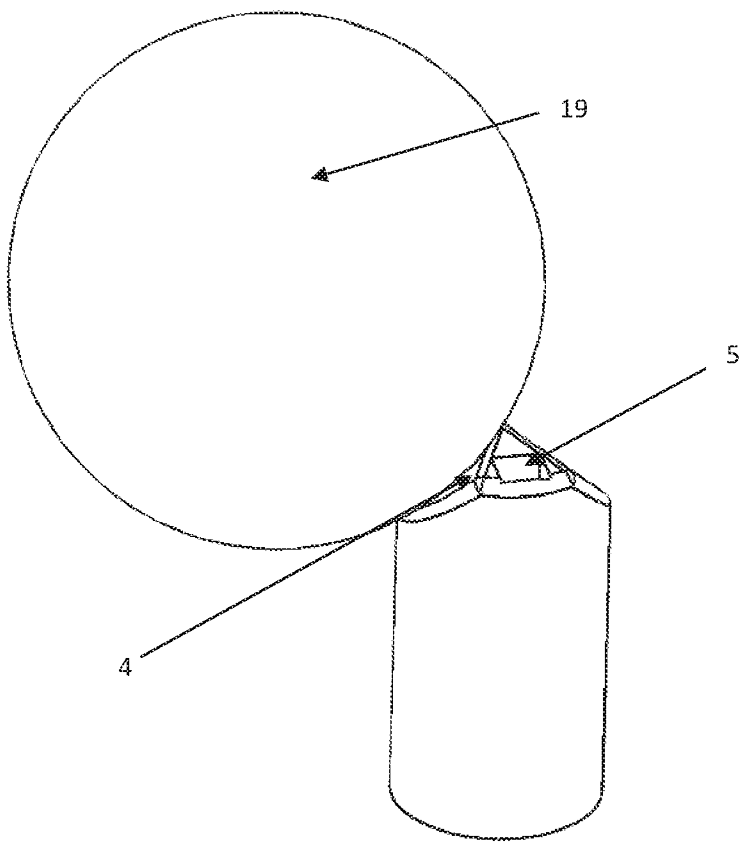

FIG. 7E shows the device of FIG. A-D with a stone 19 engaged in the exit of working channel 4. As shown, the placement of the camera 5 above the plane of the working channel 4 results in the camera having an unobstructed view of the field even when a stone 19 is engaged with the device.

Now referring to FIG. 8A-D, shown are detailed schematics of the rotation angles of the device of FIG. 7A-E in different planes. The present disclosure is not limited to particular angles or direction of rotation of various device components. The configurations shown in FIGS. 7 and 8 are for illustrative purposes only. Nor is it necessary that the exit of the working channel in devices shown in FIGS. 7 and 8 be on a plane or planar.

Figure 8A:
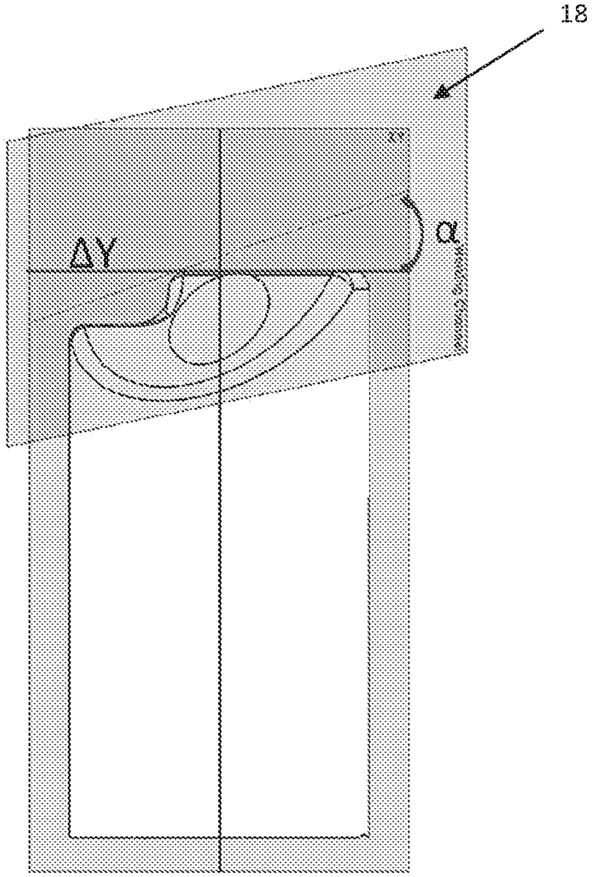
FIG. 8A-D show alternative embodiments of devices of the present disclosure.

FIG. 8A shows a view of the device of FIG. 7A-E in two dimensions on the XY plane. The exit of the working channel 4 is on a plane 18. The angle where plane 18 intersects the XY plane of view is labelled as $\alpha$. The change in height of plane 18 relative to the plane of the camera 5 is shown as $\Delta Y$.

Figure 8B:
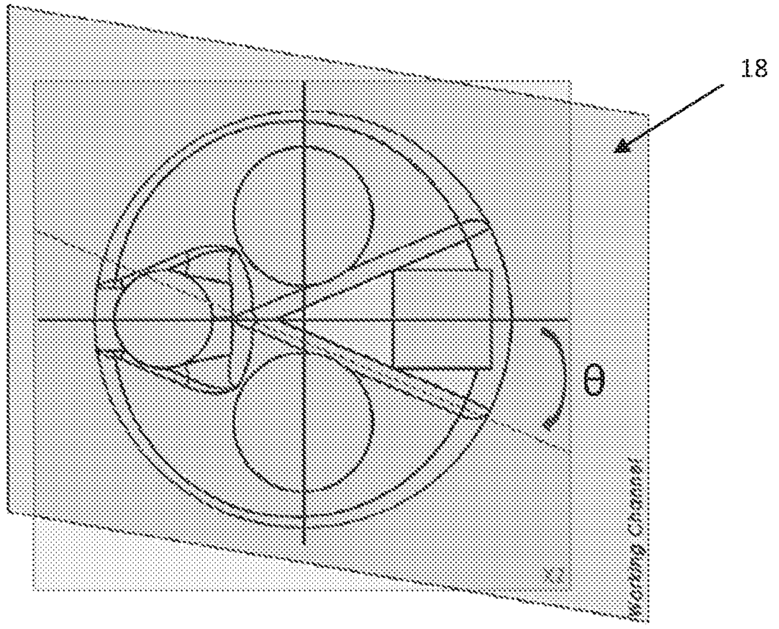

FIG. 8B shows a view of the device of FIG. 7A-E in two dimensions on the XZ plane. The angle where plane 18 intersects the XZ plane of view is labelled as $\theta$.

Figure 8C:
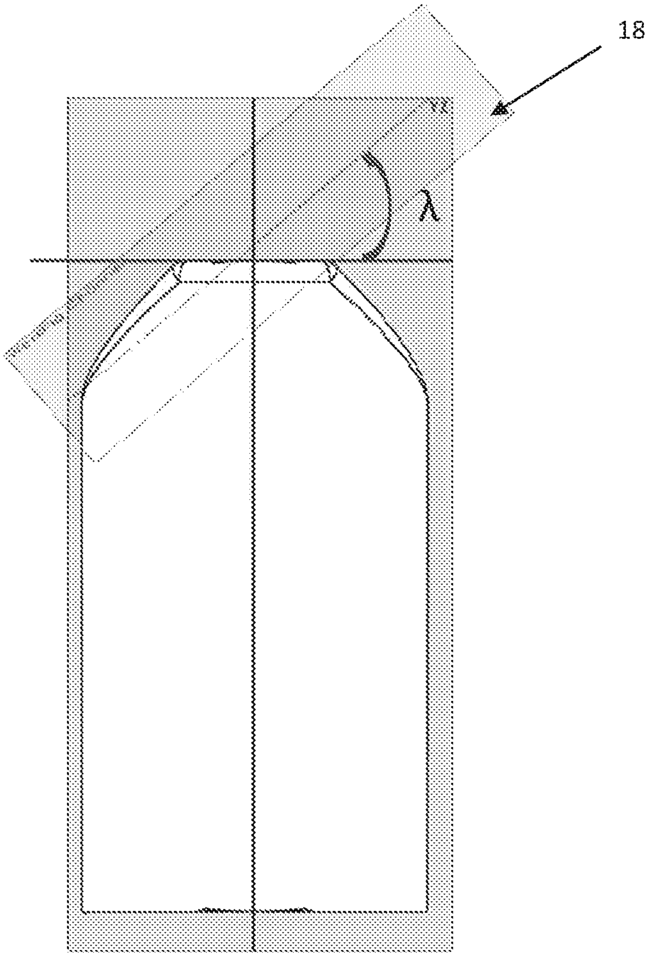

FIG. 8C shows a view of the device of FIG. 7A-E in two dimensions on the YZ plane. The angle where plane 18 intersects the YZ plane of view is labelled as $\lambda$.

Figure 8D:
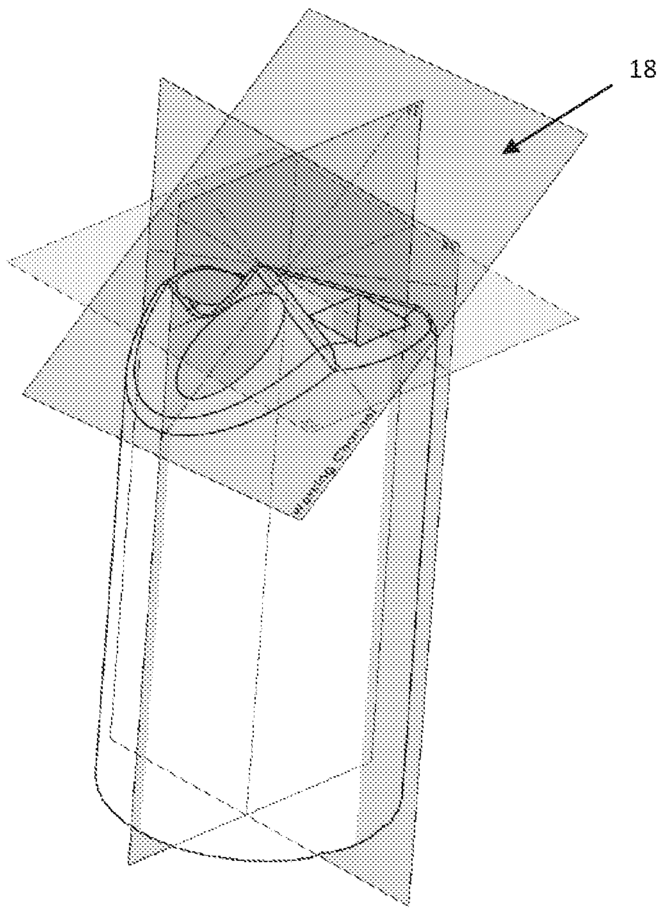

FIG. 8D shows a three-dimensional view of the device with the working channel plane 18 shown with the XY, XZ, and YZ, planes. This image shows the rotation and corresponding rotation angles of the working channel plane 18 relative to each of the other planes.

Figure 9A:
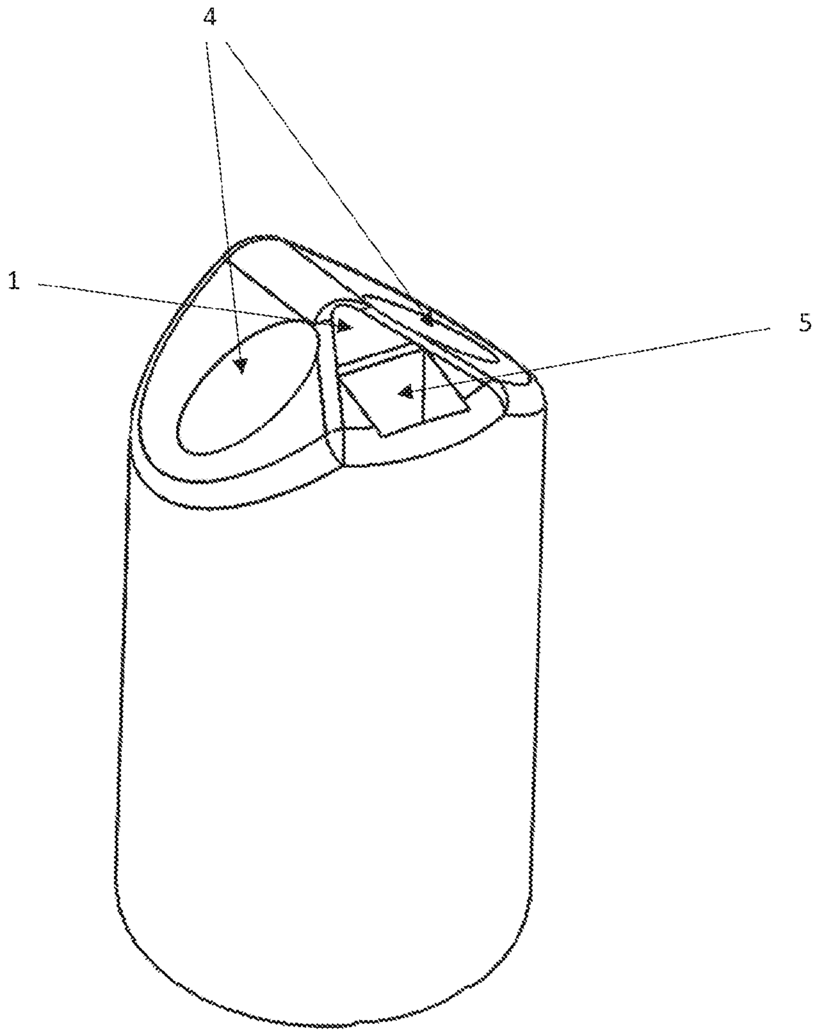
FIG. 9A-B show alternative embodiments of devices of the present disclosure.
Figure 9B:
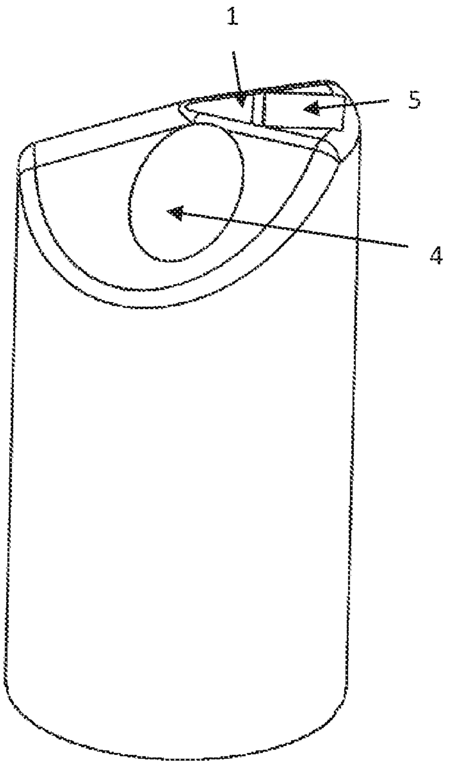
Figure 10:
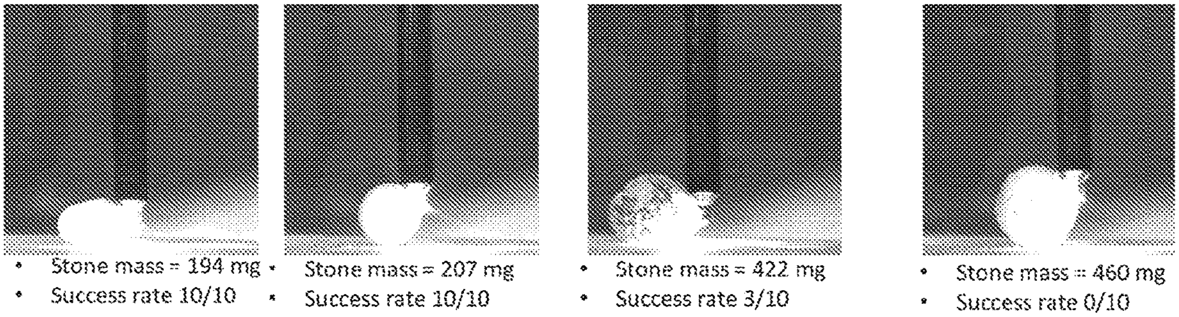
FIG. 10 shows a comparison of suction of model kidney stones using an existing ureteroscope (A) and a device of embodiments of the present disclosure.
Figure 10:
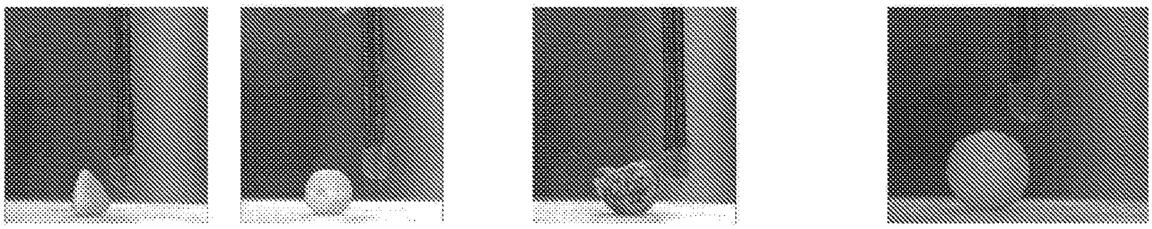

Now referring the FIG. 9A-B, shown are alternative embodiments of devices with different configurations of light 1. In FIGS. 1-8, the light is illustrated as a circular light in a discrete location. However, additional shapes, designs, and configurations of lighting for devices described herein are specifically contemplated. Some examples are described herein.

FIG. 9A shows a top view of a device with a non-circular shaped light 1 (shown in FIG. 9A as a triangle, although other shapes are specifically contemplated). Still referring to FIG. 9A, the light is shown adjacent to camera 5, although other locations are specifically contemplated. It is contemplated that placing the light 1 adjacent to the camera 5 (e.g., on a plane above the working channels) may improve illumination of the field of view when a stone is engaged with the suction port.

FIG. 9B shows a side view of the device of FIG. 9A. The light 1 is shown as a triangle adjacent to camera 5. In FIG. 9B, the exit of working channel 4 is shown on a different plane than light 1 and camera 5. In this embodiment, the light 1 and camera 5 are on a plane perpendicular to the longitudinal axis of the device and the exit of working channel 4 is on a different plane, although other configurations are specifically contemplated.

The present disclosure is not limited to the light configurations shown in the drawings. In some embodiments, all or part of the device tip is illuminated instead of having a discrete light port. In some embodiments, fiber optics where the light is transmitted through the scope to the distal end of the tip are utilized to illuminate all or part of the device tip. In some embodiments, at least part of the tip is constructed from a translucent or transparent material (e.g., a colorless thermoplastic), such that the light is transmitted through the tip and illuminates the kidney for visualization. Different areas of the tip may also have a frosted surface such that the light from the fiberoptic fiber strategically disperses out and illuminates the kidney.

The ureteroscope tip is constructed of any suitable material. In some embodiments, the tip is constructed of rigid materials such as including but not limited to, a thermoplastic, metal, or a combination thereof. Alternatively, at least part of the ureteroscope tip may be constructed of a compliant softer material such as, including but not limited to, a silicone elastomer, thermoplastic elastomer, or a foam. For example, in some embodiments, the region around the entrance of the suction port is constructed from a compliant material (shown as optional element 6 in FIGS. 1A and 3A-B), which can at least partially deform to fit the shape of the kidney stone the user is manipulating for repositioning. In some embodiments, this region is raised up from the ureteroscope tip surface (FIG. 1D) or integrated into the tip surface (FIG. 1A).

In some embodiments, the compliant material has a Shore Hardness of between OO10 and A40 (See e.g., U.S. Pat. Nos. 1,770,045 and 2,421,449; each of which is herein incorporated by referent in its entirety for a discussion of Shore hardness). The Shore hardness is determined using a Shore durometer, which is a device for measuring the hardness of a material, typically of polymers, elastomers, and rubbers. Higher numbers on the scale indicate a greater resistance to indentation and thus harder materials. Lower numbers indicate less resistance and softer materials. The ASTM D2240-00 testing standard calls for a total of 12 scales, depending on the intended use: types A, B, C, D, DO, E, M, O, OO, OOO, OOO-S, and R. Each scale results in a value between 0 and 100, with higher values indicating a harder material. Each scale uses a different testing foot on the duronieter.

In some embodiments, other parts of the tip have a hardness greater than A40. The compliant region is, for example, formed out of a solid piece of material or have porosity or be hollow or a combination thereof.

In some embodiments, the suction port comprises one or more anti-clog elements. In some embodiments, the suction port comprises an anti-clog inlet shaped such that it impedes or prevents stone fragments that may get clogged within the suction tubing. This can be done, for example, by making the suction port opening more restrictive than the inside diameter of the suction tubing (e.g., by narrowing the opening, having a mesh across the opening, or having a bar or beam in front of the opening). In some embodiments (e.g., FIG. 2C), the anti-clog element comprises a plurality of protrusions or depressions 10 that prevent stones from occluding the suction port 2.

The suction port 2 and working channel 4 can be in any configuration or used interchangeably. For example, they can be oriented across or distal from each other (FIG. 1A-D) or next to each other (FIG. 2C) or another configuration.

Existing ureteroscopes and other devices rely on dedicated channels for either irrigation or suction of fluid. Especially for ureteroscopes, there is a need to minimize the outer diameter of the device since a smaller diameter ureteroscope reduces the trauma to the patient when the device is inserted into the ureter. Ureteroscope devices typically have outer diameters of approximately between 7-10 (e.g., 8-10) French (Fr). However, the smaller the outer diameter becomes, the less room there is to fit multiple dedicated working channels (e.g., one for irrigation and one for suction).

Accordingly, in some embodiments, provided herein is a device that overcomes this limitation by utilizing the interstitial space inside an outer housing of the device to deliver irrigation fluid at or near the tip of the device while simultaneously using the working channel for fluid suction and/or other device components. This greatly improves visualization for the procedure while enabling a smaller device outer diameter. In practice, irrigation fluid can be pressurized and flow from an inlet port in the device handle, through the interstitial space within the ureteroscope outer housing, and exit the device through the one or more interstitial flow openings. In some embodiments, these openings are at the tip of the device to help clear away debris from the field of view, although the present disclosure is not limited to a particular location. Examples include, but are not limited to, on the top surface of the tip, the side surface of the tip, through an opening on the outer housing, or a combination thereof.

Now referring to FIGS. 12-13, shown is an alternative device configuration that utilizes an outer housing and interstitial fluid openings. In some embodiments, this configuration utilizes cutouts (e.g., interstitial flow openings) placed at or near the tip (e.g., distal end) of the device to direct pressurized irrigation fluid into the kidney without disturbing the small stone fragments (e.g., improving popcorn lithotripsy efficiency). In some embodiments, this configuration utilizes cutouts (e.g., interstitial flow openings) placed at or near the tip of the device to direct pressurized irrigation fluid into the kidney to clear the small stone fragments (e.g., improving visualization). The outer housing serves as a pseudo-working channel for fluid delivery or suction. Herein, a pseudo-working channel is a channel that allows for fluid delivery and/or suction but cannot accommodate instrumentation exchanges such as passing a laser fiber or basket through the channel during the procedure since there is not a direct channel or tube connecting the interstitial flow opening(s) to a port outside of the patient (e.g. in the device handle). In some embodiments, irrigation fluid is pumped in between the inner surface of an outer housing and the outer surface of an inner working channel (e.g., via a fluid port). In some embodiments, fluid is removed through the interstitial space between the outer housing and the inner working channel (e.g., via a suction port). In some embodiments, both irrigation and suction are interchangeably applied through the interstitial space between the outer housing and the inner working channel. In some embodiments, the interstitial space and the working channel are substantially (e.g., completely or partially) fluidly separate.

Figure 12A:
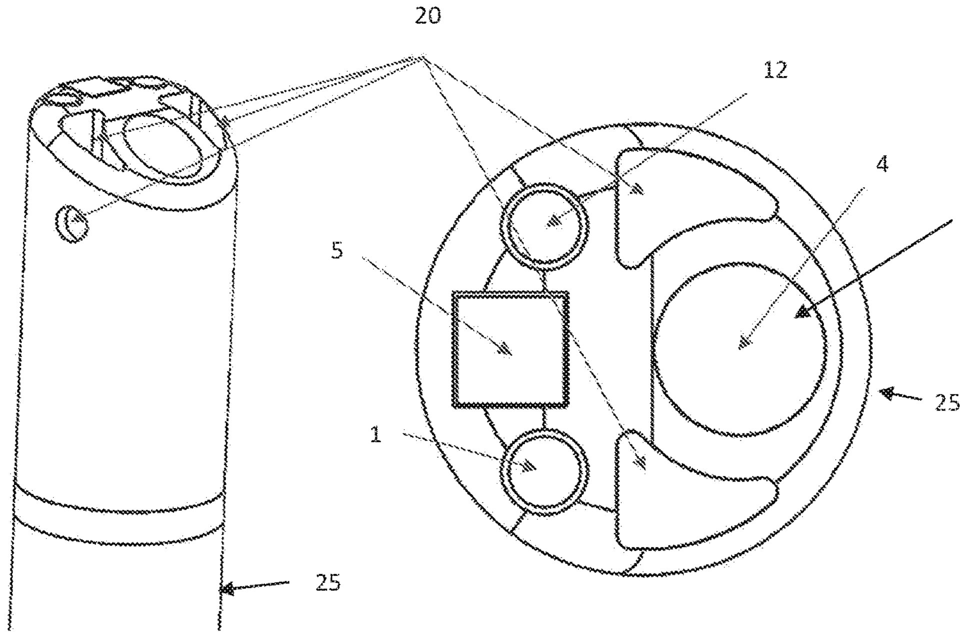
FIG. 12A-J show alternative embodiments of devices of the present disclosure.

FIG. 12A shows perspective (left panel) and top (right panel) views of a device comprising interstitial flow openings 20. FIG. 12 shows two interstitial flow openings 20 located on the distal end of the device and one on the side. However, the present disclosure is not limited to such a number or configuration of interstitial flow openings 20. For example, in some embodiments, devices comprise one or more (e.g., 1, 2, 3, 4, 5, or more) interstitial flow openings 20. The interstitial flow openings are placed in any suitable location including but not limited to, on the tip or side of the device. FIG. 12A further shows outer housing 25, light 1, working channel 4, camera 5, and pressure sensor 12.

The present disclosure is not limited to a particular material for outer housing 25. In some embodiments, outer housing is constructed of one or more materials commonly used in ureteroscopes (e.g., a flexible polymer, a metal such as stainless steel, a rigid plastic, and/or a laser cut or electrical discharge manufacturing (EDM) cut hypotube).

Figure 12B:
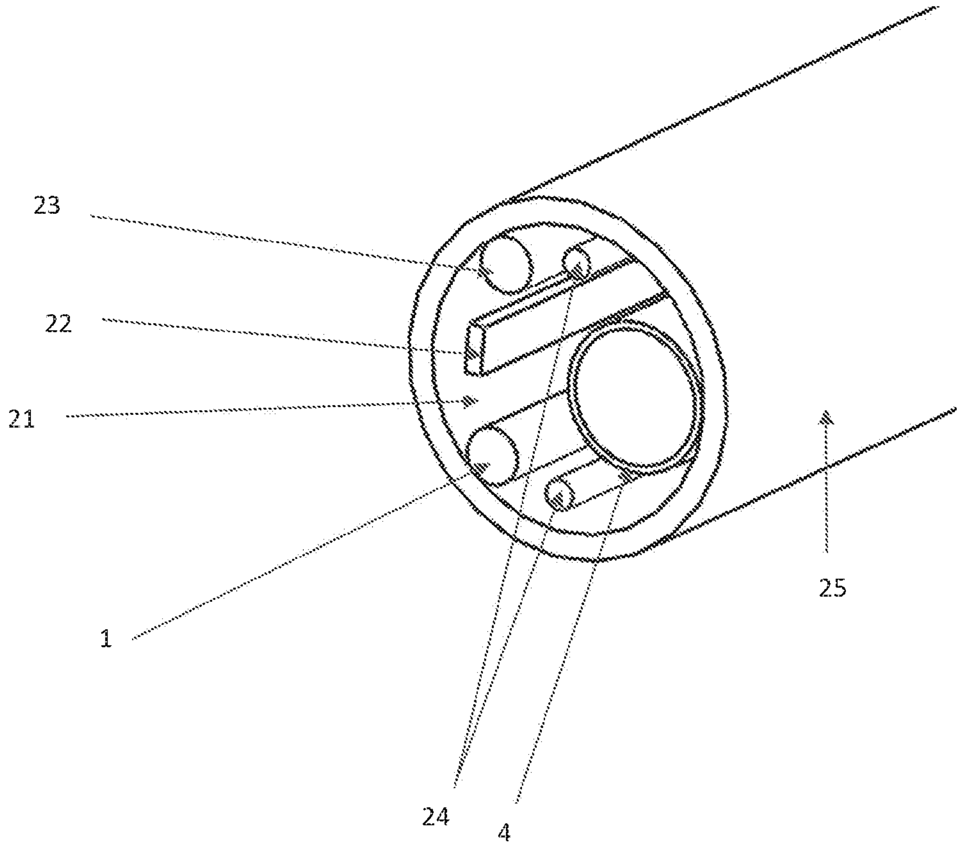

FIG. 12B shows a cut-out view of the tip of the device shown in FIG. 12A. FIG. 12B illustrates an outer housing 25 surrounding interstitial space 21. As described above, in some embodiments, the interstitial space 21 serves as a conduit to deliver irrigation to the working field (e.g., through interstitial openings (not shown in FIG. 12B) or to provide suction. The interstitial space 21 further provides a location for device components such as, for example, including but not limited to, pressure sensor wire 23, camera wire 22, and pull wires 24 (e.g., articulation pull wires). In some embodiments, interstitial space 21 further provides a location for articulation elements to allow the navigation of the tip via pull wires 24. Also shown is working channel 4 and light 1.

Figure 12C:
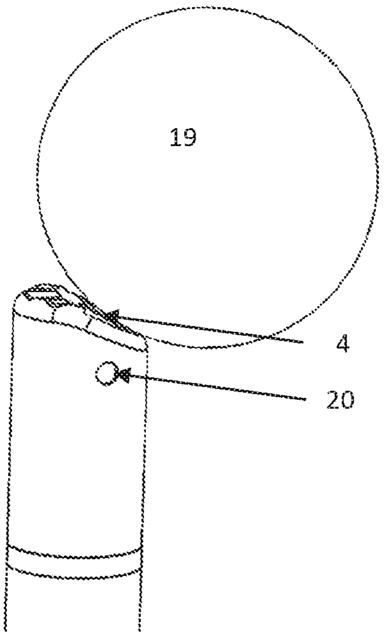

FIG. 12C shows a view of the device of FIG. 12A-B with stone 19 engaged with working channel 4. As shown in FIG. 12C, an interstitial flow opening 20 is placed on the side of the device. In the embodiment shown in FIG. 12C, the interstitial flow opening 20 is outside the area where the stone is engaged with the device, although the flow opening 20 may be placed in other suitable locations.

Figure 12D:
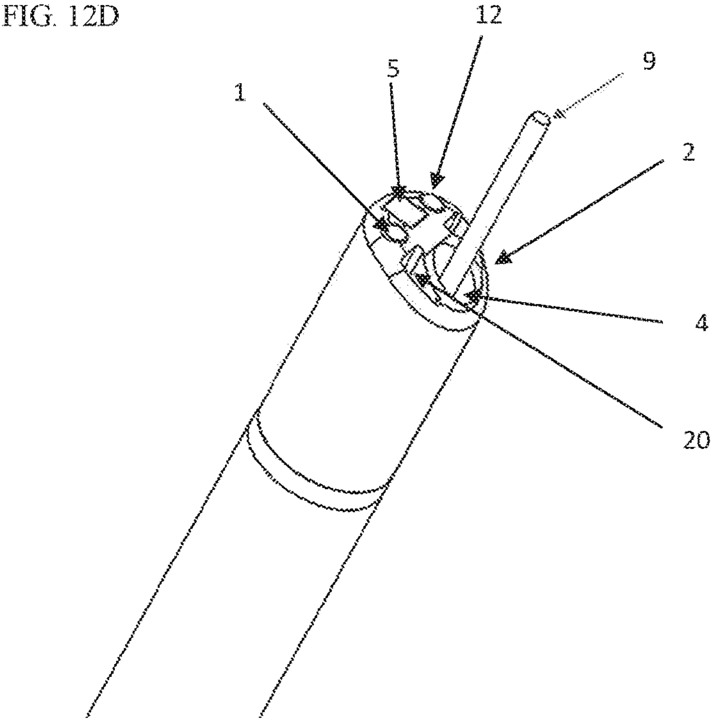

FIG. 12D shows a view of the device of FIG. 12A with laser fiber 9 protruding from working channel 4 and suction port 2. FIG. 12D further shows interstitial flow openings 20, light 1, camera 5, and pressure sensor 12. When in use, the laser 9 does not block camera 5 or light 1. Interstitial openings 20 can provide irrigation and/or suction when laser 9 is in use.

Figure 12E:
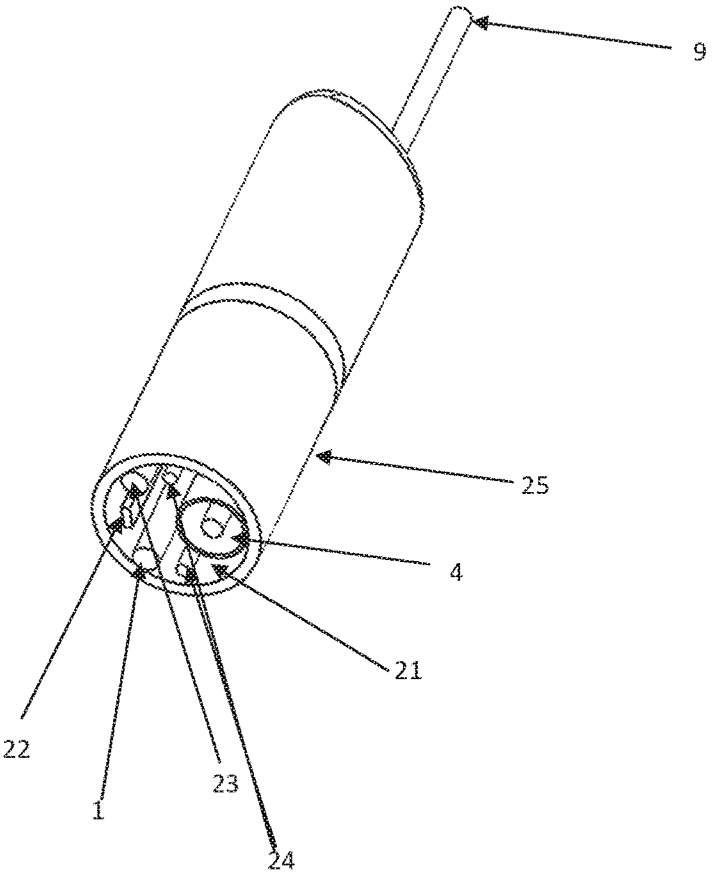

FIG. 12E shows a view of the device of FIG. 12B with laser fiber 9 protruding from working channel 4. Working channel 4 is distinct from interstitial space 21, which provides a location for light 1, pressure sensor wire 23, camera wire 22, and pull wires 24. Thus, the design of FIG. 12A-E provides two distinct channels suitable for suction and/or fluid delivery (e.g., working channel 4 and interstitial space 21) that are not in fluid communication with each other.

FIGS. 12F-J show a device that utilizes multiple working channels and an interstitial space. In some embodiments, by way of example, a first, smaller working channel with an inner diameter channel of ~1.5 Fr or 0.5 mm (e.g., plus or minus 5, 10, 15, 20, or 25%) is utilized for a laser fiber (~0.4 mm OD). This working channel is of small diameter (e.g., just large enough for a laser fiber) since fluid does not need to pass through this working channel. This allows the scope outer diameter to remain small. In some embodiments, a second, larger, working channel is utilized, ~3.6 Fr or 1.2 mm (e.g., plus or minus 5, 10, 15, 20, or 25%) inner diameter, to suck fluid through. In some embodiments, the interstitial flow opening includes a flow diverter (e.g., as shown in FIG. 15-17) to help prevent clogging of the larger working channel.

Figure 12F:
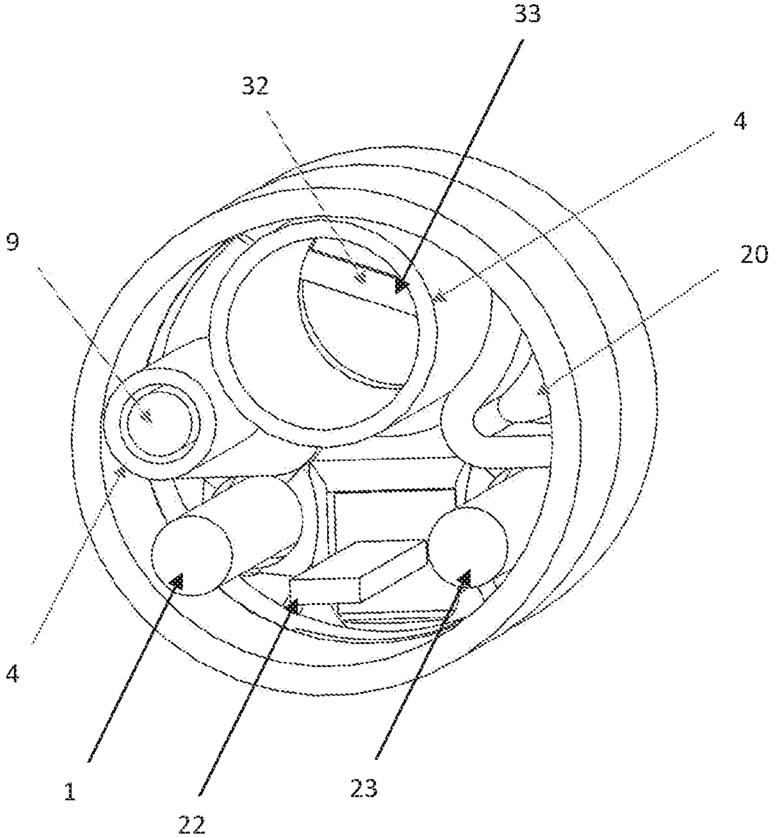

In some embodiments, the working channel optionally includes a fragment filter/mesh to prevent fragments from entering the working channel, which may clog it. In some embodiments, the filter/mesh is optionally recessed to allow for larger fragment grabbing and extraction. In some embodiments, (e.g., as shown in FIG. 12F), the filter/mesh is pivotable and/or flexible to allow an instrument to pass through/past the filter unimpeded. Then when the instrument is removed, the filter/mesh moves back into place to prevent clogging in the working channel. While the filter is illustrated on the configuration shown in FIG. 12F-J, the filter is suitable for use on any device configurations described herein.

In an alternative embodiment (not shown in FIG. 12F-J), the laser fiber is separate from any working channel and resides in the interstitial space within the pseudo working channel. In some embodiments, the laser fiber extends past the distal tip of the endoscope.

FIG. 12F shows an embodiment where the device comprises interstitial openings and more than one working channel 4 (e.g., 2, 3, 4, or more). FIG. 12F shows a cut-out view of the distal end of such a device. For illustrative purposes, FIG. 12F shows two working channels 4. Shown in FIG. 12F is one working channel 4 comprising laser 9 and a second working channel 4 (e.g., for suction) comprising an optional fragment filter/mesh 32 to prevent fragments from entering the working channel 4, which may clog it. The filter/mesh 32 shown in FIG. 12F is optionally able to pivot (e.g., around axis 33, although other configurations are specifically contemplated) to allow an instrument to pass through working channel 4. Also shown is interstitial opening 20, camera wire 22, light 1, and senor wire 23.

Figure 12G:
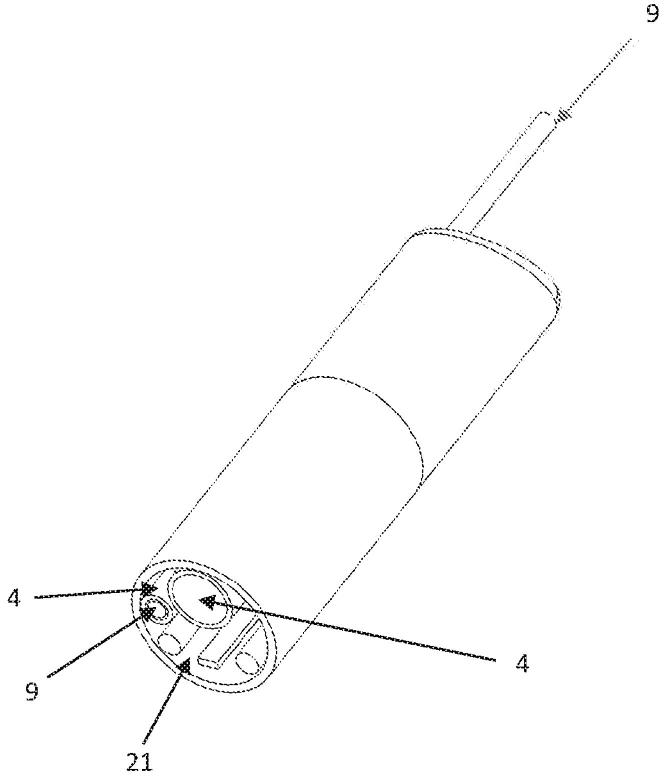

FIG. 12G shows a further cut-out view of the distal tip shown in FIG. 12F. Shown is first working channel 4 comprising laser 9 and second working channel 4 (e.g., for providing suction and/or a basket). Interstitial space 21 is in fluid communication with interstitial opening 20 (not shown in FIG. 12G).

Figure 12H:
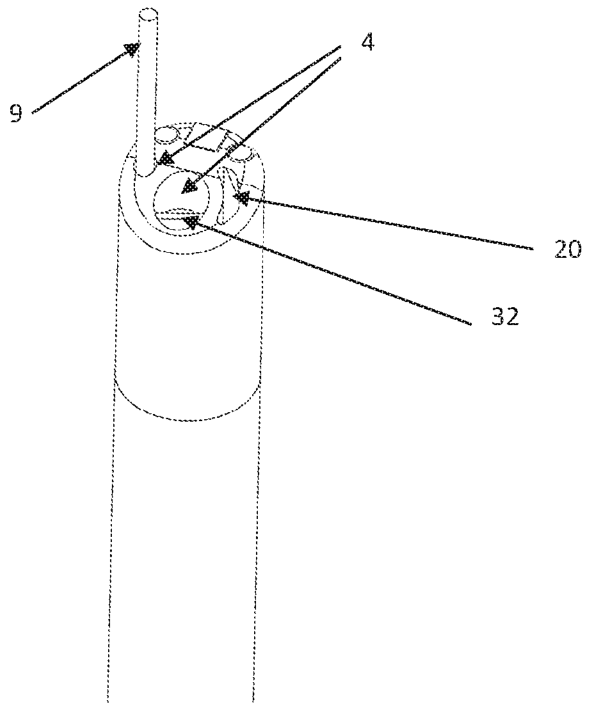

FIG. 12H shows a top view of the device of FIG. 12F. Shown is first working channel 4 comprising laser 9 and second working channel 4 (e.g., for providing suction). Also shown is interstitial opening 20. The second working channel 4 further comprises optional filter 32.

Figure 12I:
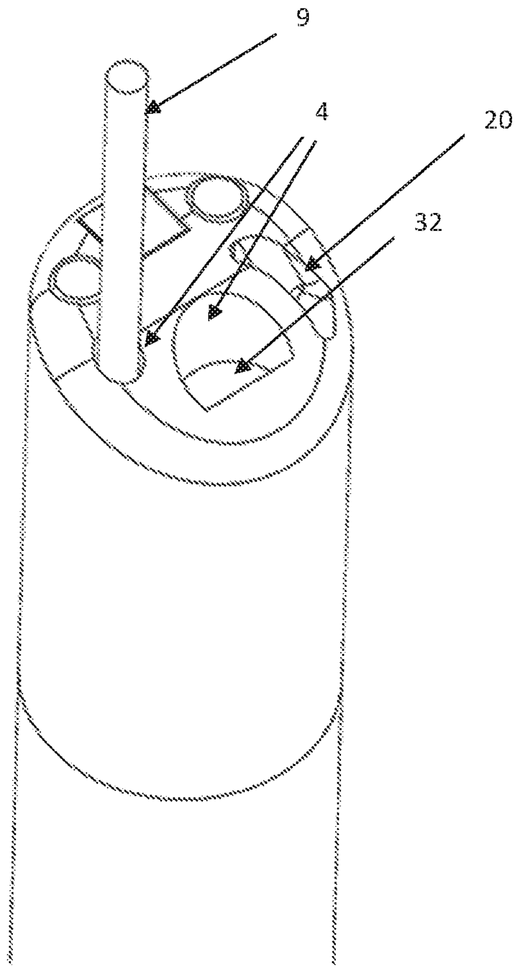

FIG. 12I shows an additional configuration of filter 32 that allows an instrument to pass through. Shown is first working channel 4 comprising laser 9 and second working channel 4 comprising filter 32. In FIG. 12I, filter 32 has a narrowed rigid opening that allows an instrument to pass through. Also shown in interstitial opening 20.

Figure 12J:
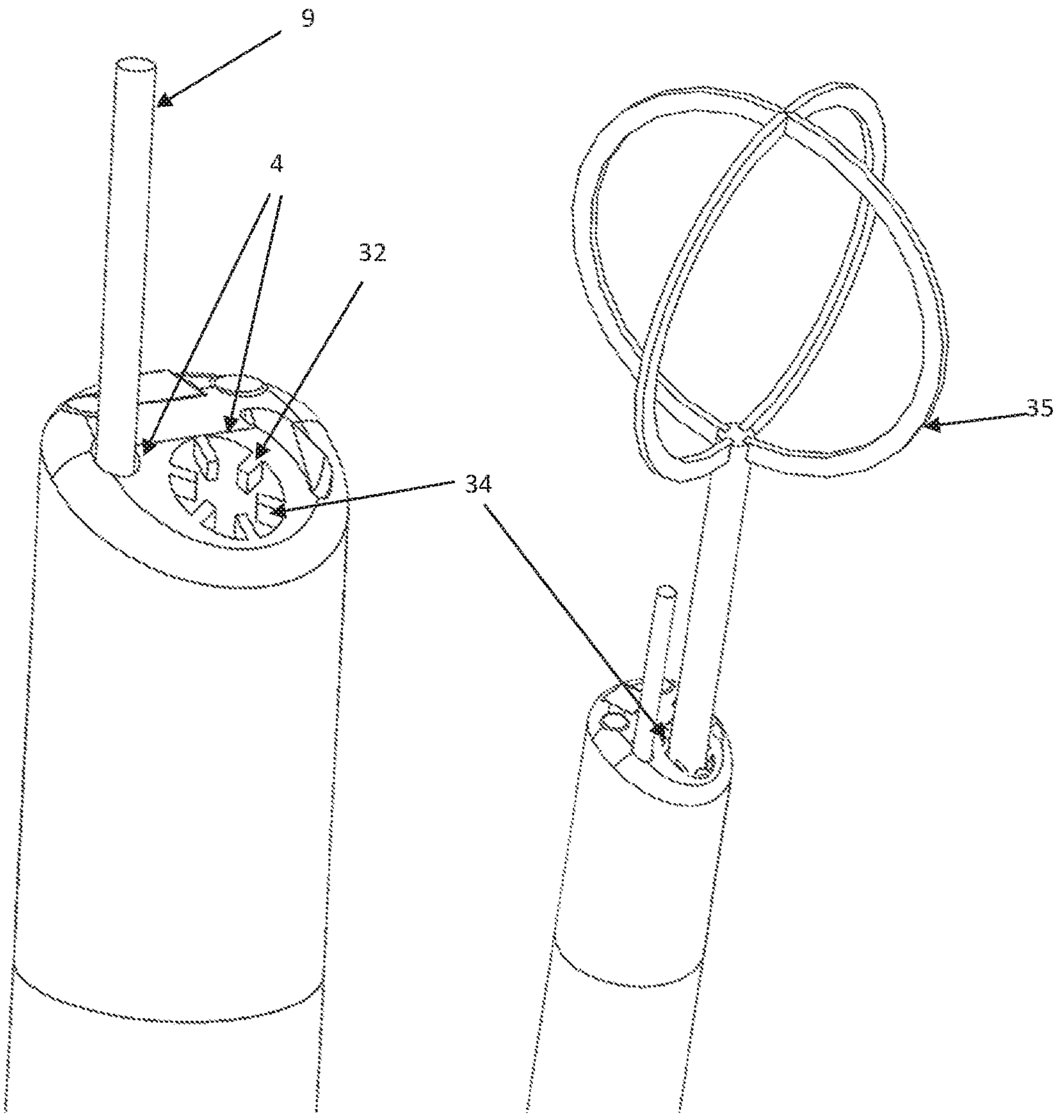

FIG. 12J shows a further configuration of filter 32 that allows an instrument to pass through. Shown is first working channel 4 comprising laser 9 and second working channel 4 comprising filter 32. In FIG. 12J, filter 32 comprises one or more elastic elements 34 that protrude in the channel. In FIG. 12J, 6 protrusions are shown, although other numbers may be utilized. The left panel shows working channel 4 and filter 32 without an instrument. When an instrument like a basket 35 is inserted (right panel), it pushes the elastomeric elements 34 out of the way so the instrument can pass in and out. Then, when no instrument is in place, the elastomeric elements spring back into place acting to partially occlude the channel opening minimizing clogging within working channel 4. In some embodiments, the elastomeric elements are composed of a material such as a thermoplastic elastomer or silicone elastomer, and have a shore A hardness between approximately 10A and 50A.

In some embodiments (e.g., those described in FIG. 12), working channel 4 is used to deliver a laser 9. However, the working channel 4 (and other channels) are also suitable for delivery of additional device components (e.g., a basket or a pair of graspers). In addition, in embodiments that utilize the interstitial space for irrigation, the working channel can be fully or partially occluded with one or more instruments while still delivering adequate irrigation at the tip of the device.

Figure 13A:
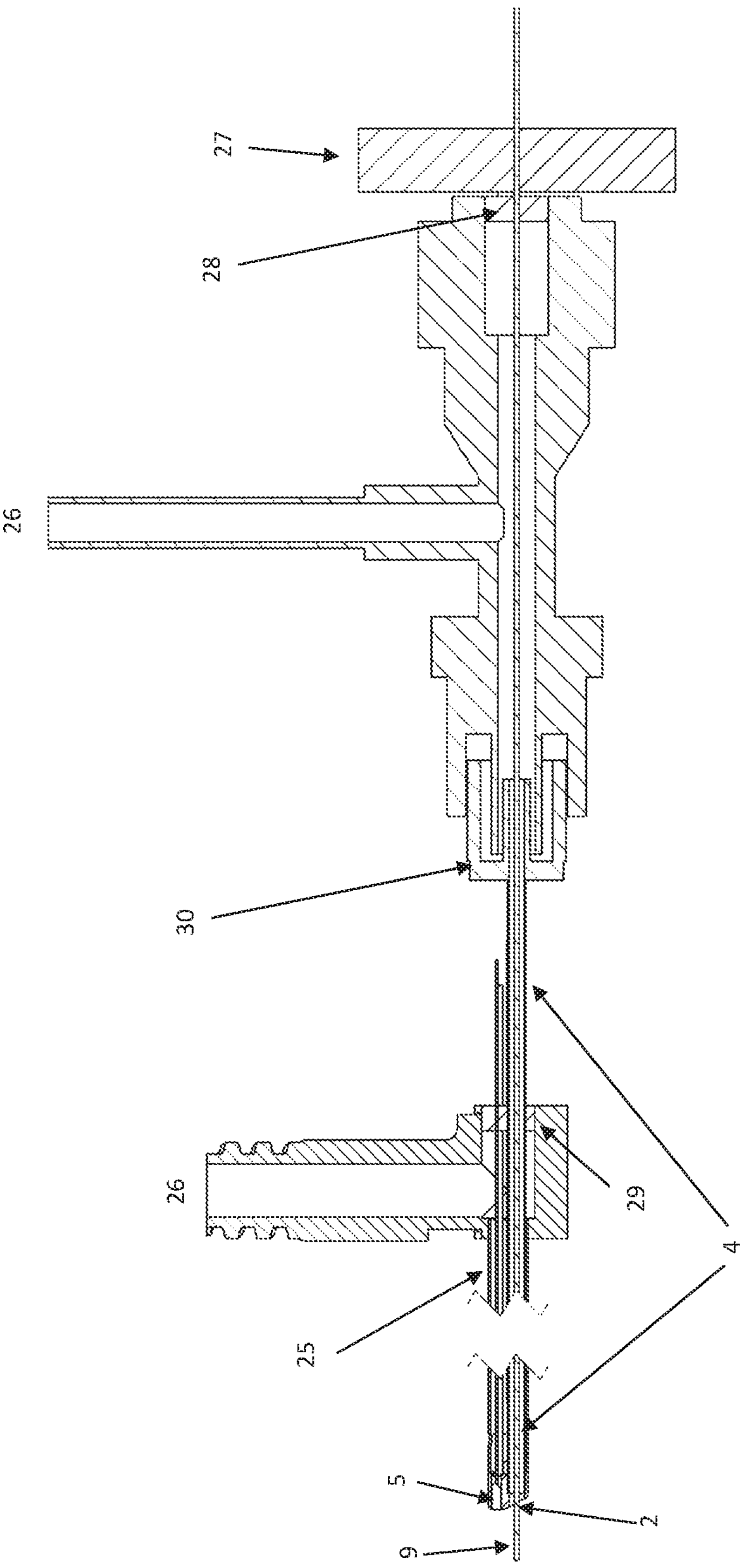
FIG. 13A-C show an alternative embodiment of a device of the present disclosure.

Now referring to FIG. 13A, shown is a section view of an exemplary device comprising an outer housing 25 and interstitial flow openings (not shown in FIG. 13A). Shown are working channel 4, suction port 2, laser 9, suction connection 30, and camera 5. Also shown in FIG. 13A is one or more fluid ports 26. The one or more fluid ports 26 are located at any suitable or convenient location on the device (e.g., the handle (not shown) or other portion of the proximal (e.g., handle) or distal (e.g., tip) end). In some embodiments, devices comprise one or more fluid ports 26 that are in fluid communication with the working channel 4 and/or interstitial space 21. For example, in some embodiments (e.g., the left fluid port 26 shown in FIG. 13A) the fluid port 26 is in fluid communication with the interstitial space 21 (not shown in FIG. 13A). The fluid port 26 provides an inlet to provide fluid and/or suction at or near the tip of the device via fluid port 26. In some embodiments, the fluid port (e.g., the right fluid port 26 shown in FIG. 13A) is in fluid communication with working channel 4.

Still referring to FIG. 13A, in some embodiments, the internal components are sealed to allow irrigation to flow through the device without damaging any internal components of the device. For example, in some embodiments, a fluid port 26 in fluid communication with the interstitial space 21 comprises a fluid seal 29 between the fluid port 26 and the outer diameter of working channel 4. Pull wires 24, camera wire 22, light 1, sensor 23 (not shown in FIG. 13A), and other components can pass through this seal. The seal prevents fluid in interstitial space 21 from flowing into the handle of the endoscope/ureteroscope device and focuses the fluid pressure toward interstitial flow opening(s) 20. Fluid seal 29 can be composed of multiple suitable materials such as, for example but not limited to, conformable elastomeric element(s), adhesive resin, adhesive resin with internal channels and sealant, or other combinations thereof. Some elements passing through fluid seal 29, such as a camera wire, may not need to translate and thus are glued/sealed into place at fluid seal 29. Other elements passing through fluid seal 29, for example pull wires for device articulation, may need to repeatedly translate proximally and distally with respect to fluid seal 29. In that scenario, it may be preferable to utilize, for example, elastomeric elements and/or a tubing channel with tight tolerance to the pull wire(s) and optionally a sealing lubricant (e.g., medical grade silicone grease), to generate a fluid tight seal that still allows translation of select components about the fluid seal 29. In some embodiments, a fluid port 26 in fluid communication with working channel 4 comprises laser fiber seal 28. In some embodiments, laser fiber seal 28 provides a fluid seal between the laser 9 and working channel 4. This focuses the vacuum pressure at the fluid port 26 to pull fluid through the suction port 2 opening, through the working channel 4, and into a fluid collection tank (not shown in FIG. 13A). In some embodiments, laser fiber seal 28 is composed of an elastomeric element and can be selectively loosened or tightened to allow repositioning of the laser 9.

Figure 14:
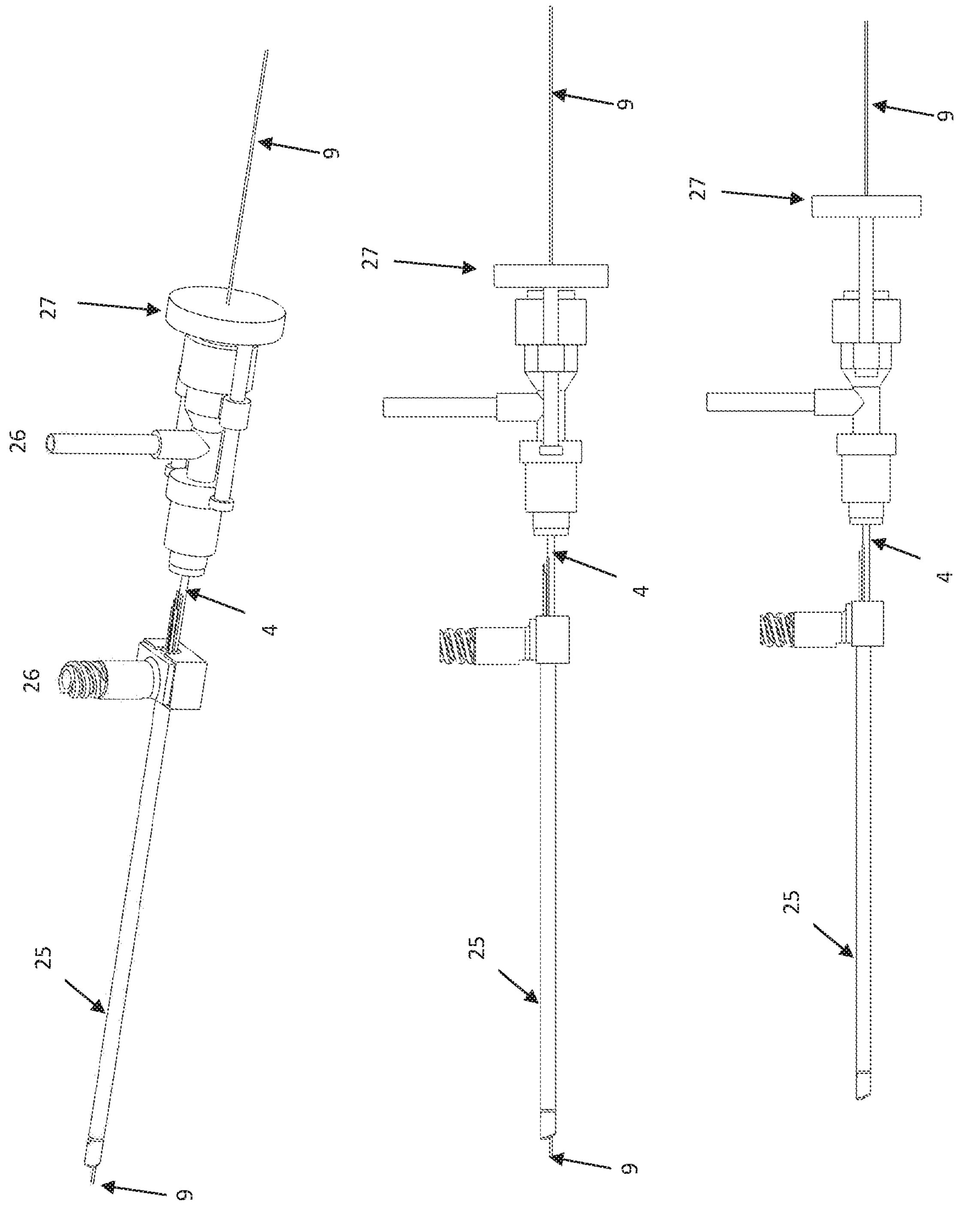
FIG. 14 shows an alternative embodiment of a device of the present disclosure.

Still referring to FIG. 13A, shown is laser slider 27 (described in detail in FIG. 14). In some embodiments, laser slider 27 is used to optionally linearly actuate the laser fiber (e.g., in the plane of the ureteroscope). This can help unclog any stone fragments from the working channel 4 that may potentially build up and limit the suction flow.

Figure 13B:
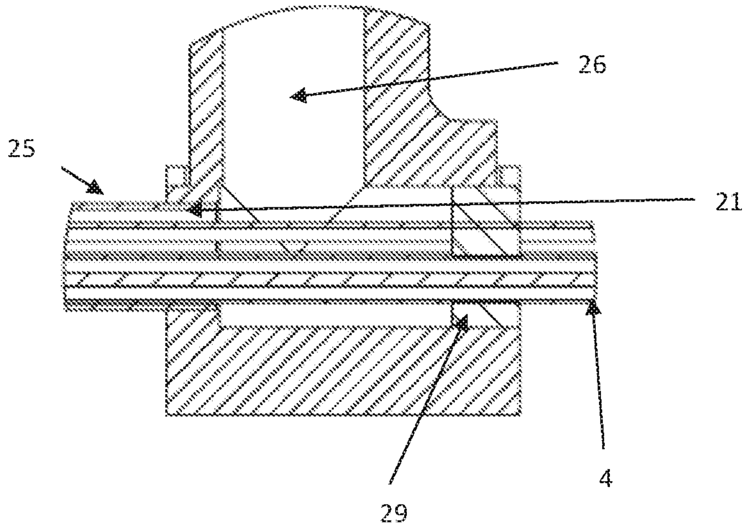

FIG. 13B shows a close-up view of fluid seal 29. Fluid seal 29 fluidly isolates working channel 4 from the labeled fluid port 26. In FIG. 13B, fluid port 26 is in fluid communication with interstitial space 21 and is fluidly sealed to outer housing 25.

Figure 13C:
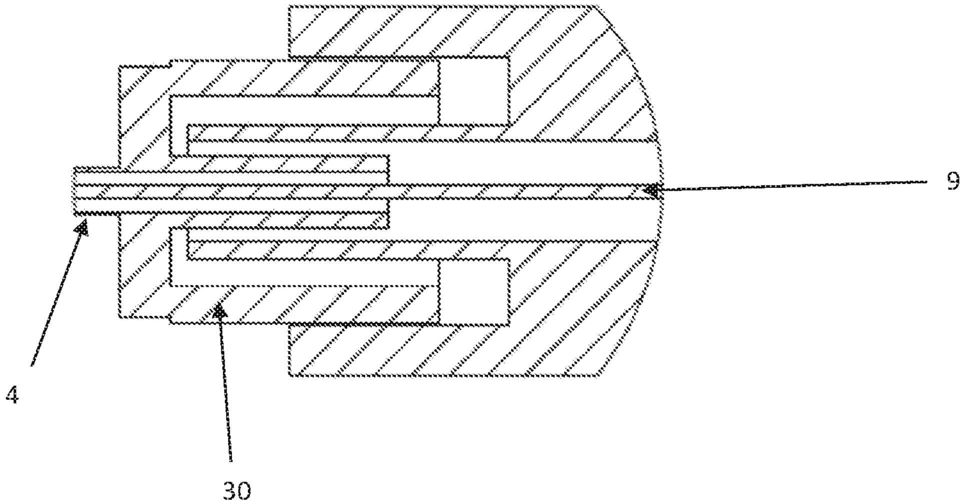

FIG. 13C shows a close-up view of suction connection 30. Suction connection 30 fluidly connects working channel 4 (comprising laser fiber 9 in FIG. 13C) to a fluid port 26 (not shown in FIG. 13C). Suction connection 30 isolates working channel 4 from interstitial space 21. In the embodiments shown in FIG. 13C, fluid port 26 is not in fluid communication with interstitial space 21.

In some embodiments, devices of the present disclosure (e.g., comprising outer housings, fluid ports, and interstitial spaces and other element described herein) are constructed de novo. In some embodiments, a commercially available ureteroscope or other devices designed to be used laparoscopically are modified to include such elements (e.g., including but not limited to, those available from Dornier MedTech, Munich, Germany or Richard Wolf, Vernon Hills, IL). In some embodiments, existing devices that comprise outer housings are utilized. In some embodiments, a fluid port is added to the device and the internal components are sealed to allow irrigation to flow from the fluid port (e.g., located on the handle) to the tip of the scope through the existing interstitial space. In some embodiments, one or more interstitial flow openings are added to the tip of the device to allow irrigation to be pumped into the kidney or other location. In some embodiments, this irrigation is pumped in without disturbing any stones or stone fragments present.

Now referring to FIG. 14, shown is an embodiment of a device comprising a laser slider 27. FIG. 14 shows a device of FIG. 12-13 comprising a laser slider. However, the laser slider can be integrated into any number of devices described herein. The top view of FIG. 14 shows a device comprising laser slider 27, fluid ports 26, working channel 4, outer housing 25, and laser 9. The middle view of FIG. 14 shows laser slider 27 in normal configuration (e.g., not in use). It is pushed forward and the tip of laser 9 extends beyond the distal tip of the ureteroscope so it can ablate kidney stones. In the bottom view of FIG. 14, laser slider 27 is actuated to move laser fiber 9 proximally toward the ureteroscope handle. The laser slider 27 can then be returned to its original position to move the laser fiber back into proper position for kidney stone ablation. In some embodiments, the actuation is repeated one or more times in order to dislodge any stones in working channel 4.

Now referring to FIG. 15-18, shown are alternate configurations of devices that comprise flow diverters in or adjacent to the irrigation/suction/working channels. In some embodiments, the flow diverter directs irrigation flow towards, across, and/or through a suction opening (e.g., working channel). In some embodiments, the flow diverter functions as a fluidic particle filter. For example, directing irrigation flow near or across the suction opening redirects or filters out larger stone particles or fragments, which could tend to clog or obstruct the suction channel. For example, with a 3.6 Fr (1.2 mm) diameter working channel, a 0.4 mm diameter laser fiber inserted into the working channel, and suction being pulled on the working channel, it is advantageous to only allow stone fragments or particles that are below approximately 0.3 mm in diameter to enter the device working channel, although different size channels are specifically contemplated. This helps to ensure that the particles are sucked through the working channel and out of the scope without having to remove the laser fiber. This is advantageous from a procedural standpoint since the clinician does not have to pause the lithotripsy procedure in order to clear their vision of particles floating in their field of view.

It is also useful to balance the irrigation flowrate and the suction flowrate. A higher irrigation rate pushes particles and fragments away from the scope/suction opening, while a higher suction flowrate pulls particles and fragments toward the scope/suction opening. For kidney stone dusting, preferred irrigation rates are approximately 15-30 ml/min and preferred suction rates are approximately 8-17 ml/min. However, these rates can change depending on the geometry of the tip and the procedural scenario in which the device is used.

Figure 15A:
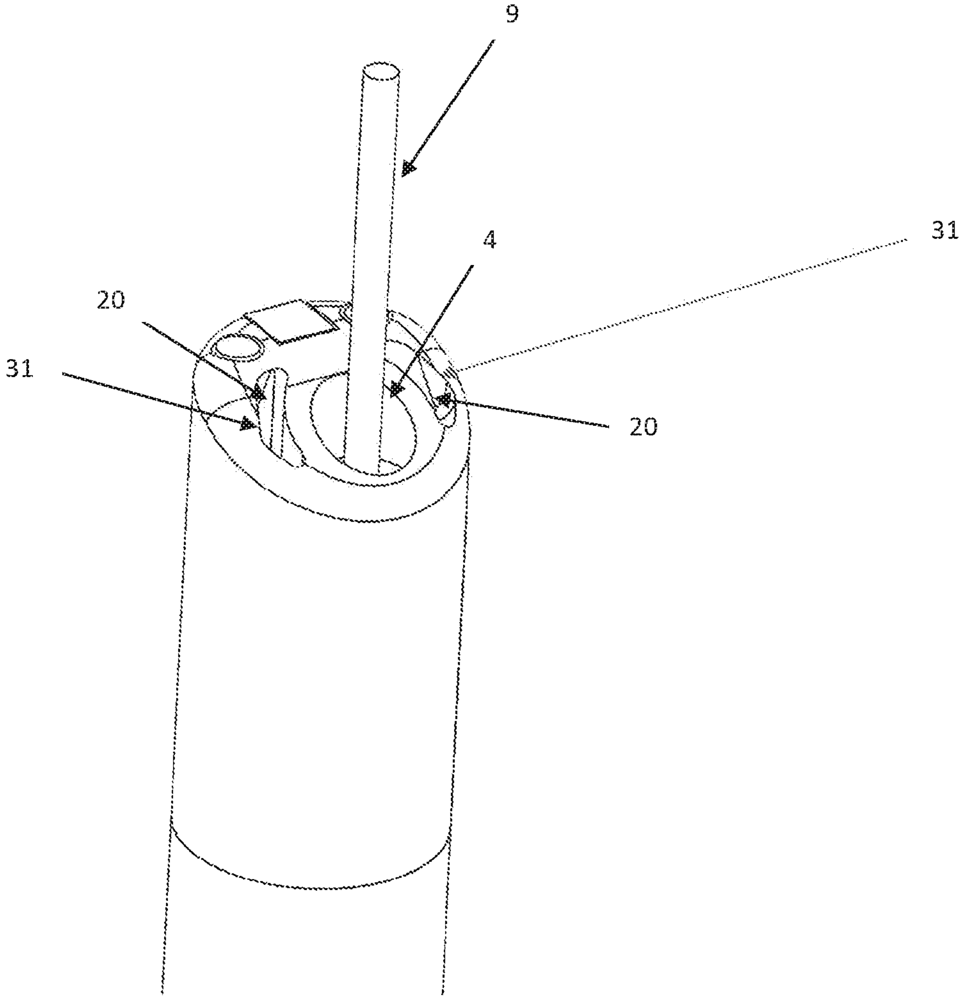
FIG. 15A-B show alternative embodiments of devices of the present disclosure.

FIG. 15A shows a device comprising exemplary flow diverters 31. In FIG. 15A, the flow diverters 31 are located adjacent working channel 4 comprising laser fiber 9. FIG. 15A also shows interstitial openings 20 (e.g., to provide irrigation). In FIG. 15A, flow diverter 31 are located at the opening of interstitial opening 20. Flow diverters 31 are configured to direct irrigation (e.g., provided through interstitial openings 20) towards the suction opening (e.g., working channel 4 comprising laser 9). In the embodiment shown in FIG. 15A, two interstitial openings 20 and 2 flow diverters 31 are shown, although other configurations are specifically contemplated.

Figure 15B:
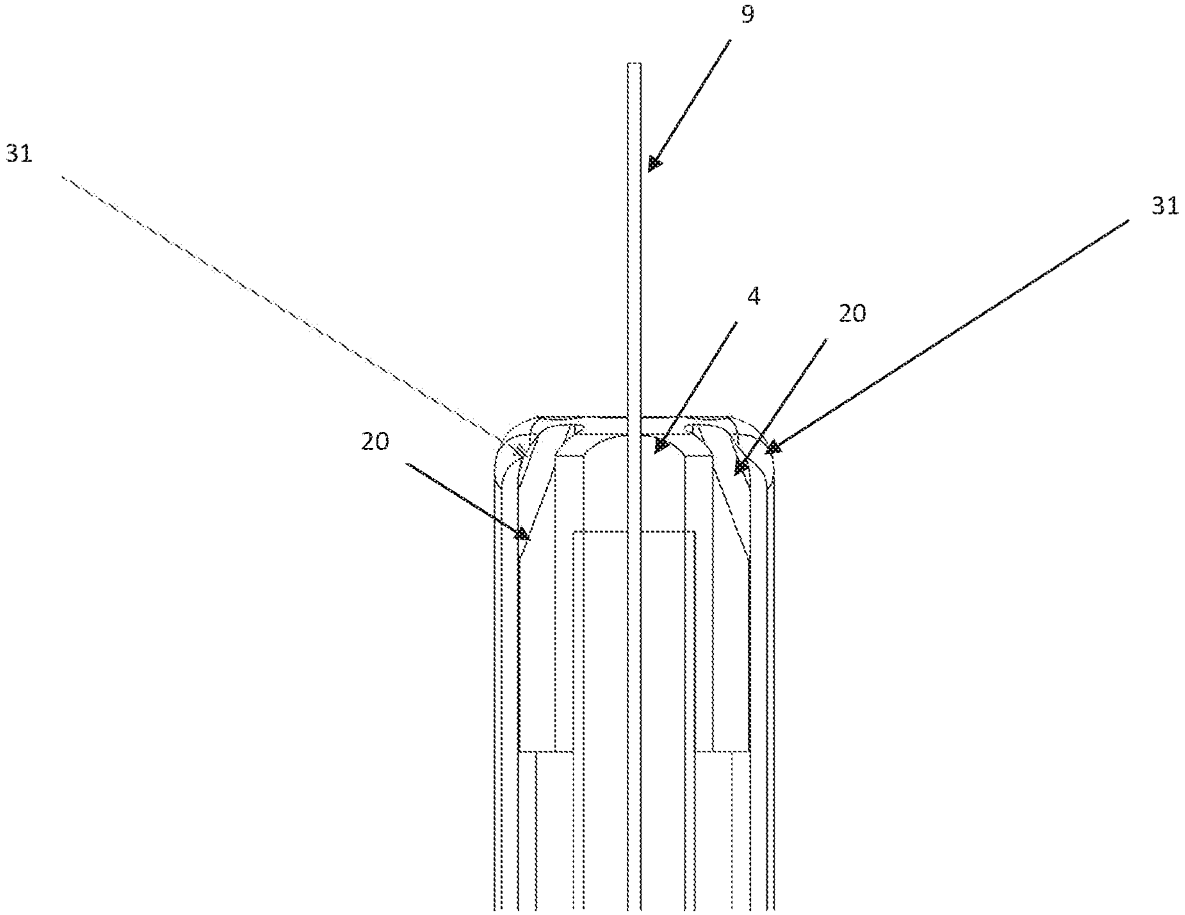

FIG. 15B shows a cut-out side view of FIG. 15A. As shown, the flow diverters 31 are located at the interstitial opening 20. However, the present disclosure is not limited to interstitial openings. Other channels may be utilized to deliver irrigation and/or suction. In the embodiments shown in FIG. 15B, irrigation is provided through the interstitial opening 20 adjacent flow diverters 31 and is directed by flow diverter 31 towards working channel 4.

Figure 16A:
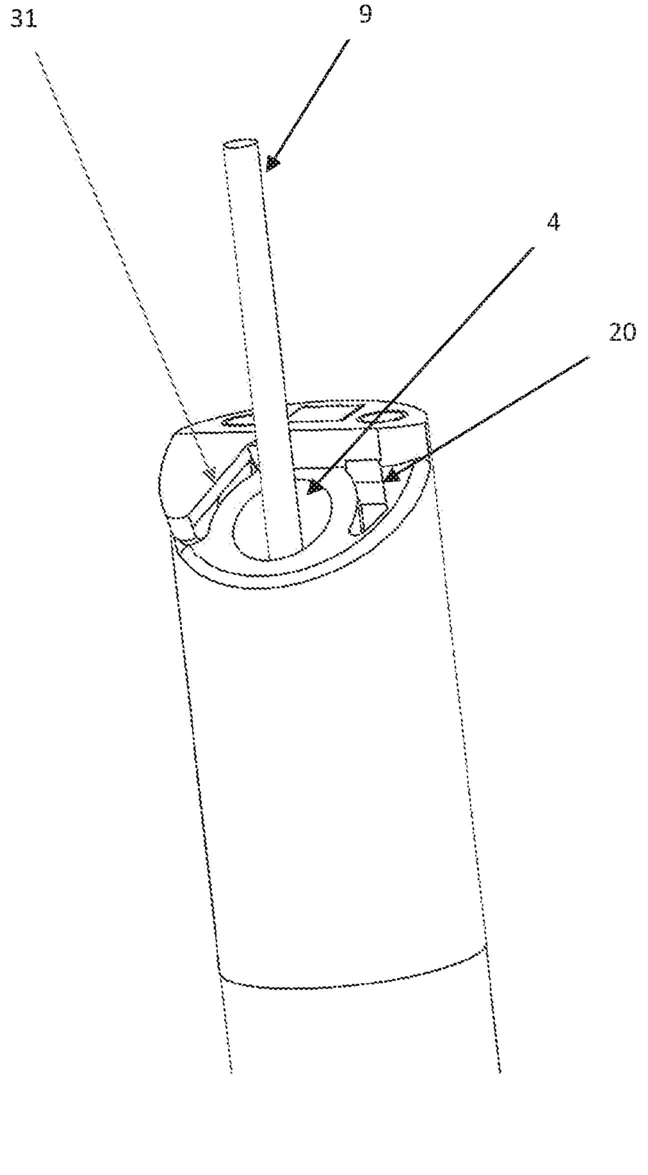
FIG. 16A-B show alternative embodiments of devices of the present disclosure.

FIG. 16A shows an embodiment where the flow diverter 31 protrudes from the distal face of the tip of the device to direct the irrigation flow across or partially across the working/suction channel 4. The flow diverter 31 shown in FIG. 16A is flush with the outside face of the tip of the device and has perpendicular sides adjacent to working channel 4. However, the present disclosure is not limited to the geometry shown in FIG. 16A. It is contemplated that other shapes of flow diverter 31 are functionally equivalent. Also shown in FIG. 16A is interstitial opening 20 and laser 9.

Figure 16B:
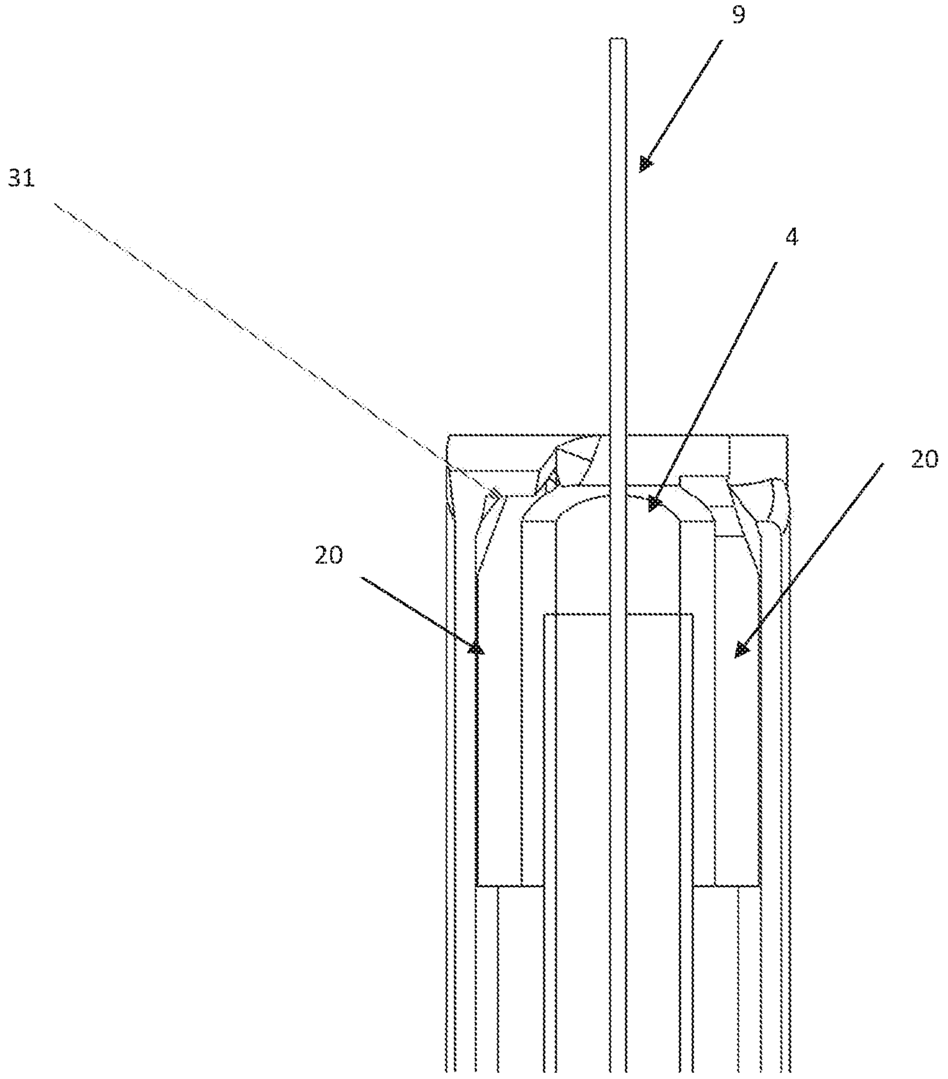

FIG. 16B shows a cut-out side view of FIG. 16A. Flow diverter 31 is located at interstitial opening 20 on the left side of the view shown in FIG. 16B. The flow diverter 31 does not block opening 20. In the embodiments shown in FIG. 16B, irrigation is provided through the interstitial opening 20 adjacent flow diverter 31 and is directed by flow diverter 31 towards working channel 4.

Figure 17A:
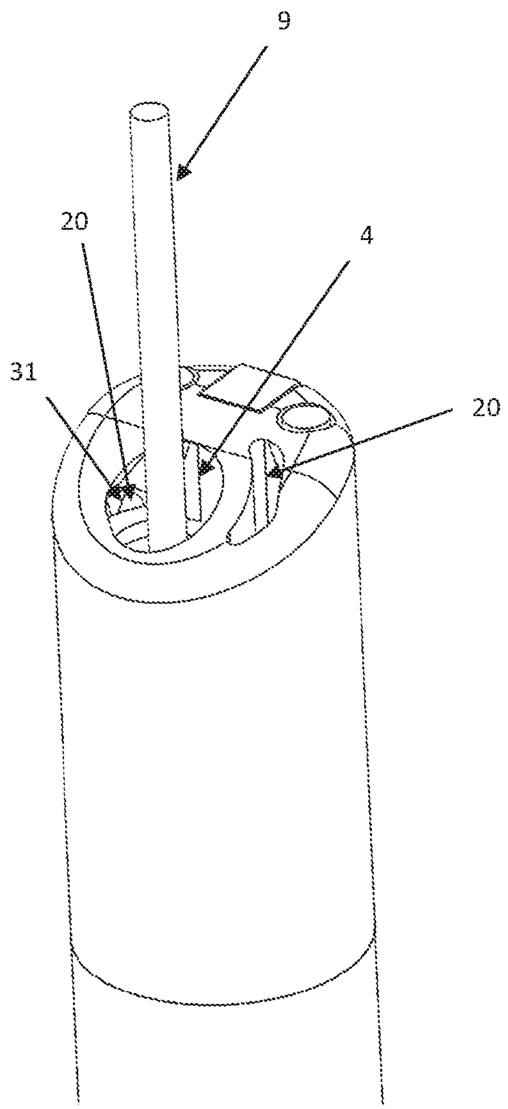
FIG. 17A-B show alternative embodiments of devices of the present disclosure.

FIG. 17A shows an embodiment where flow diverter 31 opens up to the working/suction channel 4 (e.g., comprising laser 9). Also shown in FIG. 17A are two interstitial openings 20. Flow diverter 31 directs fluid from interstitial opening 20 on the left side in fluid communication with flow diverter 31 to working channel 4.

Figure 17B:
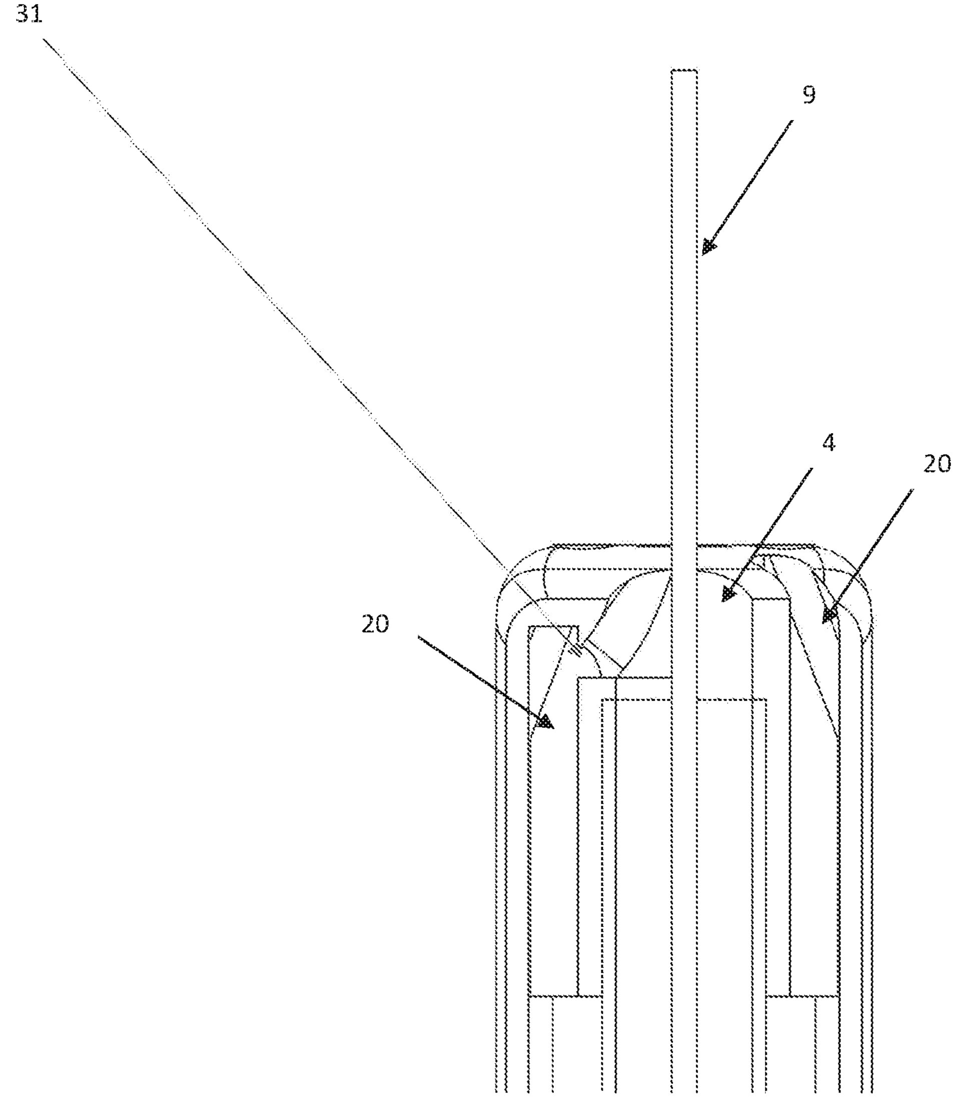

FIG. 17B shows a cut-out side view of FIG. 17A. Flow diverter 31 is located at interstitial opening 20 on the left side of the view shown in FIG. 17B, which is in fluid communication with working channel 4. In the embodiment shown in FIG. 17B, irrigation is provided through the interstitial opening 20 adjacent flow diverter 31 and is directed by flow diverter 31 towards working channel 4. In some embodiments, flow diverter 31 is composed of similar materials to that of the ureteroscope/endoscope tip. For example, this material may be a form of thermoplastic or metal. In some embodiments, flow diverter 31 is molded integrally with the rest of the device tip or is attached as a separate component.

Figure 18A:
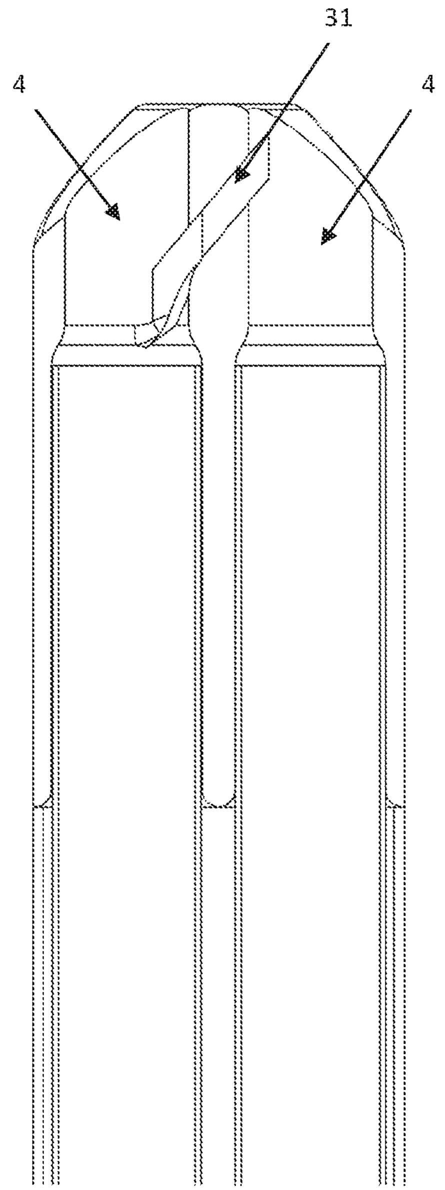
FIG. 18A-C show alternative embodiments of devices of the present disclosure.

FIG. 18A shows a side cut-out view of a device comprising a flow diverter 31 that links two working channels 4. The device shown in FIG. 18A lacks interstitial openings. Instead, irrigation is provided via a working channel 4. The flow diverter then directs flow of irrigation fluid from one working channel 4 towards the second working channel (e.g., comprising a suction component). In the embodiment shown in FIG. 18A, the flow diverter is angled from an upper opening to a lower opening.

Figure 18B:
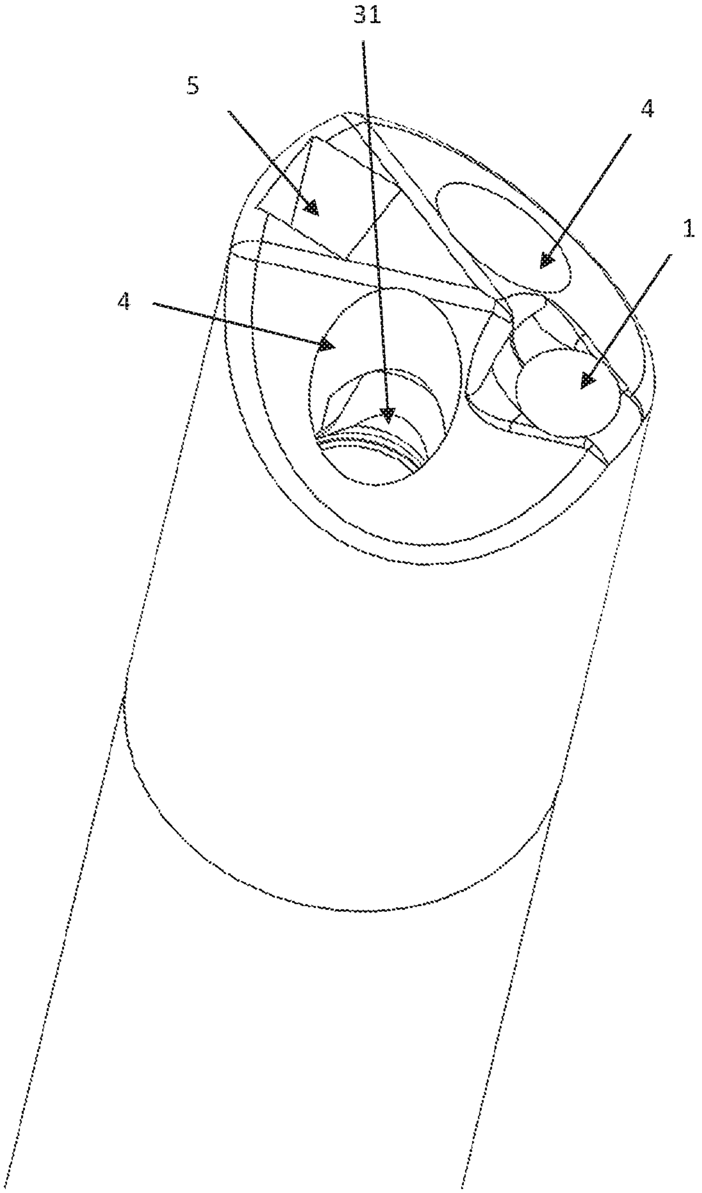

FIG. 18B shows a top view of the device of FIG. 18A. Shown is the lower opening of flow diverter 31 into working channel 4 (the upper opening of flow diverter 31 in the second working channel 4 is not shown). Also shown are light 1 and camera 5.

Figure 18C:
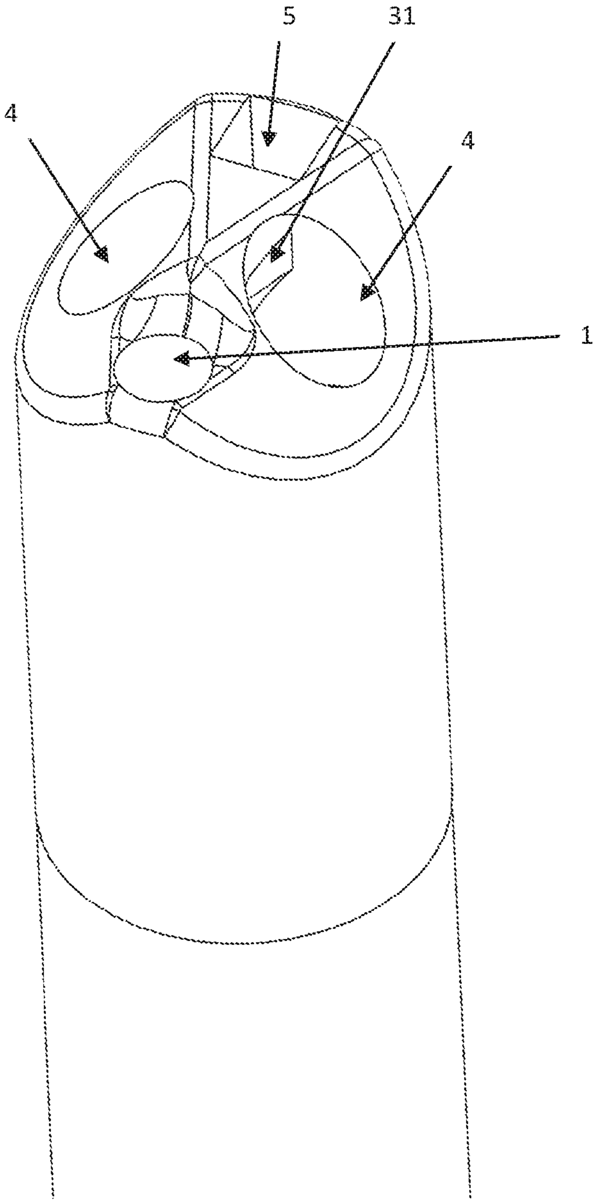

FIG. 18C shows a top view of the device of FIG. 18A. Shown is the upper opening of flow diverter 31 into working channel 4 (the lower opening of flow diverter 31 in the second working channel 4 is not shown). Also shown are light 1 and camera 5.

The present disclosure is not limited to the flow diverters described herein. In some embodiments, additional geometries and configurations of flow diverters are utilized. For example, in some embodiments, a combination of two or more (e.g., 2, 3, 4, 5, or more) flow diverters are utilized. In some embodiments, if more than one flow diverter is utilized, they are the same or different. In some embodiments, flow diverters are symmetrically or asymmetrically located on the distal tip of the device. In some embodiments, flow diverters are located adjacent an interstitial opening and/or working or other channel or port. In some embodiments, a device comprises channels with and without flow diverters.

The present disclosure is not limited to geometries or physical features of flow diverters. In some embodiments, the flow diverter comprises one or more physical features that divert an irrigation fluid stream in a direction other than perpendicular to the long axis of the device tip. In some embodiments, a flow diverter includes a structure, such as, for example, an angled channel opening, overhang, undercut, channel link (e.g., where one working channel or "pseudo working channel" is linked to another working channel or "pseudo working channel" at or near the tip), or other structure, that acts to increase flow and/or turbulence at, near, within, or across a suction inlet on the endoscope.

Figure 11:
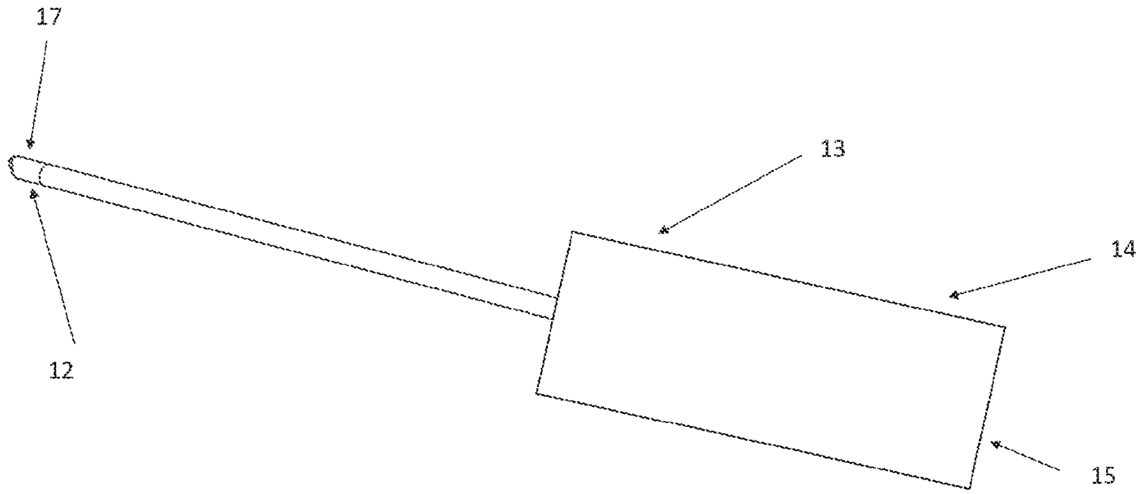
FIG. 11 shows an exemplary system of embodiments of the present disclosure.

In some embodiments, the ureteroscopes described herein are provided as part of a system. An exemplary system is shown in FIG. 11. Referring to FIG. 11, shown is a system comprising ureteroscope tip 17, temperature and/or pressure sensor 12, ureteroscope handle 13, suction port distal end 14, and working channel distal end 15. In some embodiments, the system includes an irrigation delivery system, laser, and camera (not shown in FIG. 11). In some embodiments, the system includes a mechanism to articulate the ureteroscope tip 17. In some embodiments, systems include a component configured to move suction and/or laser/irrigation delivery systems between symmetrical working channels. In some embodiments, the handle/system includes a mechanism to linearly translate the laser forward and backward with respect to the long axis of the device. This can be accomplished through a manual sliding mechanism or other means. This can be useful to unclog the device when suction is applied through working channel 4 with laser included. If a clog occurs, it will tend to occur near the entrance of the tip. By moving the laser fiber backward then forward (by about an inch), one can quickly clear any stone fragments that may have clogged or partially clogged working channel 4.

In some embodiments, the devices and systems described herein are used in combination with laser lithotripsy systems. Lasing may be performed with a pulsed Ho:YAG laser coupled to a fiber optic that can be passed through the working channel of the ureteroscope, although other systems such as a TFL system are specifically contemplated.

In use, the ureteroscope tip is inserted in the ureter of a subject. The camera and articulation mechanism is used to advance the ureteroscope to the vicinity of a stone. Once a stone is visualized, laser ablation, in combination with irrigation and suction is performed. Once the stone has been ablated and debris fragments and stone dust have been satisfactorily removed via suction, the ureteroscope is removed.

In some embodiments, the irrigation flows through the working channel/laser port in a controlled manner. In some embodiments, a component for controlling the flowrate and total amount of irrigation fluid is included. The suction port can also be dynamically adjusted to control the flowrate and total amount of fluid that is removed from the kidney. These two systems work in unison to maintain a safe pressure balance within the kidney. For example, if the tip of the ureteroscope has engaged a stone for relocation, the tip may become occluded, thus reducing the amount of fluid that can be sucked out of the kidney. In some embodiments, the system senses this reduction of fluid removal and adjusts the amount of irrigation flowing into the kidney automatically. The suction intensity can also be adjusted. For example, if more suction force is needed to pick up a kidney stone or large fragment for relocation or extraction, the vacuum pressure is increased. Alternatively, once a stone has been moved to the desired location, the vacuum pressure is reduced or eliminated so the stone is released from the ureteroscope tip. The device can also include a pressure sensor to monitor the pressure within the kidney and adjust the in/out flow of fluid accordingly.

Additionally, in some embodiments, a temperature sensor is included on the tip or near the tip to measure the temperature of fluid within the kidney. If the temperature gets too warm due to laser dusting lithotripsy, the irrigation and suction intensity automatically respond to flow in colder fluid and remove warmer fluid.

In some embodiments, systems further comprise a side port to maintain suction even when a stone is engaged. In some embodiments, the side port comprises an actuation mechanism to selectively open and close the suction side port. In some embodiments, a computer processor, computer, and display (e.g., monitor, smart phone, tablet, or smart watch) is used to operate one or more functions of the device, including but not limited to, to monitor and report temperature and/or pressure and/or move irrigation/laser and suction components between interchangeable channels. In some embodiments, a user reads the pressure and/or temperature and manually adjusts suction and/or irrigation to maintain an appropriate temperature and/or pressure. In some embodiments, the system adjusts suction and/or pressure automatically. For example, in some embodiments, the computer system both reads pressure and/or temperature, determines appropriate action, and instructs the suction and/or irrigation systems to make adjusts in flow and/or suction rate. In some embodiments, the computer system reads the temperature and/or pressure at regular intervals (e.g., multiple times per second, once per second, once every 5, 10, 30, 45, or 60 seconds, once per minute, or less often). In some embodiments, adjustments to flow and suction are continuously performed in order to keep temperature and pressure parameters within an acceptable range. For example, in some embodiments, temperature is maintained below 43 to 50° C. and intrarenal pressure is maintained below 40 cm $H_2$0.

The pressure sensor can be used to monitor the balance between fluid irrigation and suction. For example, it may be preferable to maintain a certain pressure in the kidney to distend the kidney prior to laser lithotripsy. However, too much pressure in the kidney can be detrimental to the patient. During kidney stone laser lithotripsy, it is preferable to maintain a suction at or below approximately 40 ml/min. In general, the greater the suction rate, the larger the size of stone fragment that will get sucked into the working channel. By keeping the suction rate at or below 40 ml/min (e.g., below 20 ml/min), the stone fragments or particles that are sucked into the working channel will tend not to clog the device, hence it is preferably not to exceed this suction rate. By measuring the pressure at or near the tip, the system can adjust the suction and irrigation to the desired level. The system can also include an option to momentarily increase the suction amount (for example by pressing a button on the handle of the ureteroscope) to a pressure capable of exceeding a suction rate of, for example, 40 ml/min. This momentary high suction amount can potentially be ideal for the picking and placing of stone fragments to different areas of the kidney. During this time, the irrigation flow could automatically compensate for any changes in suction flowrate to maintain an ideal pressure. Then when the doctor wants to release the stone fragment, they can select to reduce or eliminate the suction flow, thus releasing the stone.

EXAMPLES

The following examples are illustrative, but not limiting, of the devices, systems, and methods of the present invention. Other suitable modifications and adaptations of the variety of conditions and parameters normally encountered in clinical therapy and which are obvious to those skilled in the art are within the spirit and scope of the invention.

Example 1

An experiment was performed that compared a Richard Wolf Cobra ureteroscope (See e.g., U.S. Pat. No. 9,089,297) to a ureteroscope of embodiments of the present disclosure. A variety of different stone sizes were tested. The suction rate was set to 60 ml/rain through the suction channel. Then, the ureteroscope tip was lowered down to the stone such that the suction channel was in contact with the stone. The ureteroscope tip was then raised up and whether or not the stone was held onto the tip was recorded. This test was repeated 10 times with the stone being in a random orientation each time. The number of times the stone was held securely out of 10 was recorded.

The results show that while it is possible to reposition some stones using suction through the Richard Wolf Cobra scope, due to the tip shape there is difficulty picking up larger and more contoured stone fragments (particularly those above ~400 mg) (FIG. 10A). In contrast, using the device of embodiments of the present disclosure, the ability to pick up stones was significantly improved (FIG. 10B).

Figure 19:
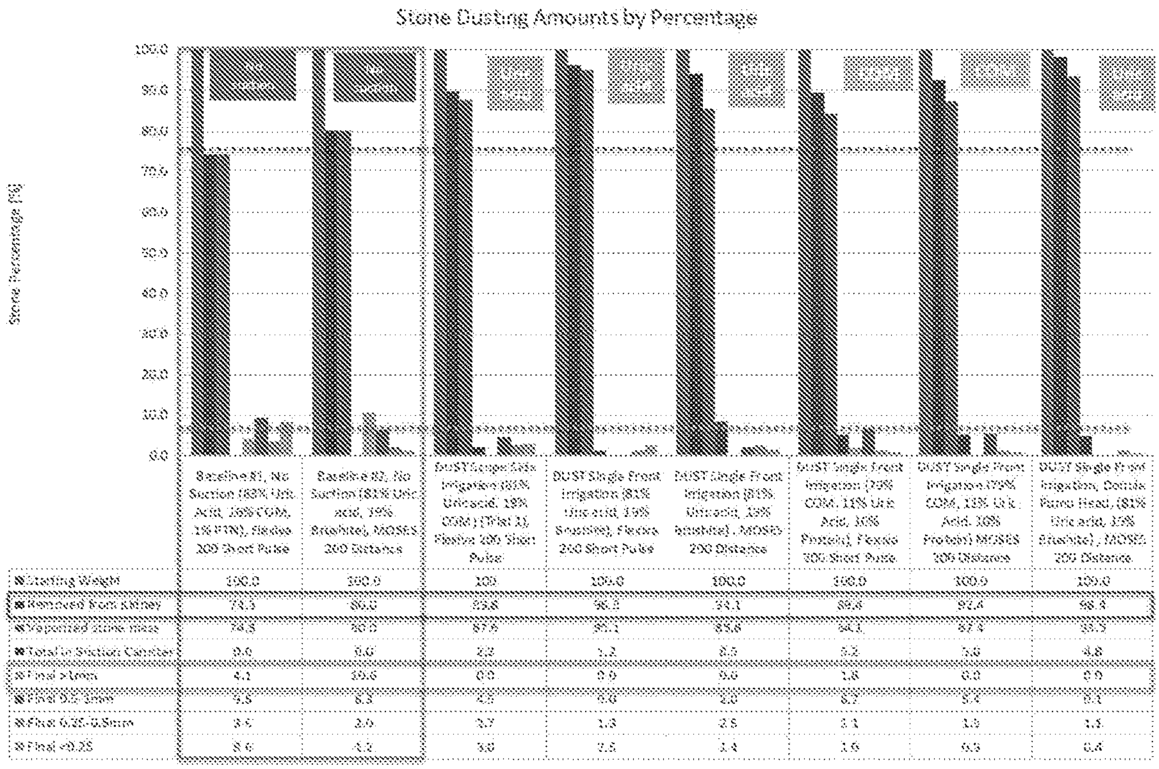
FIG. 19 shows that suction enables better stone outcomes during kidney stone removal.

Further experiments demonstrated that, by removing the small particulates in a kidney stone simulation model, there is an improvement in not only vision but stone removal from the kidney over baseline that doesn't use suction. For example, in trials using a traditional kidney stone dusting procedure with no suction, approximately 75-80% of the stone mass was removed from the kidney model. In trials that utilized the suction between about 90-99% of the stone mass was removed from the kidney (FIG. 19).

All publications and patents mentioned in the above specification are herein incorporated by reference as if expressly set forth herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

The invention claimed is:

1. An endoscopic device, comprising:

components including a suction tube defining at least a portion of a suction channel, a pull cable including a pull wire translating therein, and camera wires;

a handle at a proximal end of the endoscopic device, the handle comprising a housing defining an internal space;

a first fluid port adapted to receive fluid from a fluid source, the first fluid port comprising a proximal opening and a distal opening, wherein the components extend through the proximal opening and the distal opening;

a distal end including an outer surface and a suction port in fluid communication with the suction tube, the suction port including an opening in the outer surface, the distal end further comprising anti-clog elements comprising protrusions on the outer surface adjacent to said opening, the protrusions extending distally and configured to prevent occlusion of the suction port by forming depressions between the protrusions;

an outer housing extending distally from the handle to the distal end, the outer housing surrounding an interstitial space and portions of the components extending from the handle into the outer housing, a proximal end of the outer housing being sealingly received in the distal opening of the first fluid port, proximally of the proximal opening of the first fluid port, to establish fluid communication between the interstitial space and the first fluid port, whereby the fluid provided at the first fluid port can flow into the interstitial space and directly contact at least the suction channel and the pull cable;

an interstitial flow opening at the distal end of the endoscopic device in fluid communication with the first fluid port and the interstitial space, the interstitial flow opening configured to discharge the fluid;

a first fluid seal positioned in the handle to seal at least the suction tube and the pull cable and prevent the fluid in the interstitial space from flowing into the internal space of the handle;

a second fluid seal located proximally of the first fluid seal to seal a proximal end of the suction tube;

a laser fiber seal located proximally of the second fluid seal, a proximal portion of the suction channel extending between the proximal end of the suction tube and the laser fiber seal; and a second fluid port in fluid communication with the proximal portion of the suction channel and configured to apply suction through the suction channel.

2. The endoscopic device of claim 1, wherein said distal end further comprises one or more flow diverters, and wherein said flow diverters are configured to direct fluid flow towards the opening of the suction port.

3. The endoscopic device of claim 1, wherein the first fluid seal comprises at least one of a conformable elastomeric element and an adhesive resin.

4. The endoscopic device of claim 1, wherein the first fluid seal comprises adhesive resin.

5. The endoscopic device of claim 1, wherein the distal end of the endoscopic device further comprises a camera, and wherein the opening of the suction port is angled out and away from an optical axis of the camera.

6. The endoscopic device of 5, wherein the outer housing in a non-articulated position has a centerline that defines a Y-axis, wherein an X-axis is perpendicular to the Y-axis, wherein a Z-axis is perpendicular to the Y-axis and the X-axis, and wherein the opening of the suction port is angled at an angle of 120-160 degrees about the Y-axis of the endoscopic device.

7. The endoscopic device of claim 1, wherein the outer housing in a non-articulated position has a centerline that defines a Y-axis, wherein an XZ-plane is perpendicular to the Y-axis, and wherein the opening of the suction port is angled at an angle of 5-25 degrees about a line positioned on an XZ-plane of the endoscopic device.

8. The endoscopic device of claim 1, wherein said distal end further comprises one or more flow diverters configured to direct fluid flow towards the opening of the suction port.

9. The endoscopic device of claim 1, wherein the first fluid seal is configured to allow the pull wire to repeatedly translate proximally and distally with respect to the first fluid seal.

10. The endoscopic device of claim 1, wherein the first fluid seal is an elastomeric element and/or comprises a tubing channel with a tight tolerance to the pull wire.

11. The endoscopic device of claim 10, wherein the first fluid seal comprises a sealing lubricant.

12. The endoscopic device of claim 11, wherein the sealing lubricant comprises medical grade silicone grease.

13. The endoscopic device of claim 1, wherein the endoscopic device further comprises a working channel opening in the outer surface of the distal end, wherein the outer housing in a non-articulated position has a centerline that defines a Y-axis, wherein an XZ-plane is perpendicular to the Y-axis, wherein the opening of the suction port is angled about a line positioned on the XZ-plane.

14. The endoscopic device of claim 13, wherein the working channel opening is on a different plane than the opening of the suction port.

15. The endoscopic device of claim 13, wherein the distal end comprises a camera cut-out region extending proximally from the XZ-plane, and wherein a camera is positioned proximally of the XZ-plane.

16. The endoscopic device of claim 1, wherein the endoscopic device further comprises a working channel opening in the outer surface of the distal end, wherein the outer housing in a non-articulated position has a centerline that defines a Y-axis, wherein an XZ-plane tangential to a most distal surface of the distal end is perpendicular to the Y-axis, and wherein the opening of the suction port and the working channel opening are angled about a line positioned on the XZ-plane and positioned proximally of the XZ-plane.

17. The endoscopic device of claim 1, wherein the distal end comprises a camera cut-out region extending proximally from the XZ-plane, and wherein a camera is positioned proximally of the XZ-plane.

18. The endoscopic device of claim 1, wherein the laser fiber seal is configured to seal a laser fiber and the suction channel to focus vacuum pressure at the second fluid port to pull fluid through the suction channel.

19. The endoscopic device of claim 1, wherein the laser fiber seal is configured to be selectively loosened or tightened to allow repositioning of a laser fiber.

20. The endoscopic device of claim 1, wherein the first fluid seal is positioned in the handle to seal the proximal opening of the first fluid port, wherein the second fluid seal surrounds an outer surface of the proximal end of the suction tube, and wherein the laser fiber seal is longitudinally spaced apart from the second fluid seal.

* * * * *